(12) United States Patent
Johnson

(10) Patent No.: US 11,617,653 B2
(45) Date of Patent: *Apr. 4, 2023

(54) MAGNETIC PROSTHETIC

(71) Applicant: Stephen Bramblett Johnson, Bishop, GA (US)

(72) Inventor: Stephen Bramblett Johnson, Bishop, GA (US)

(*) Notice: Subject to any disclaimer, the term of this patent is extended or adjusted under 35 U.S.C. 154(b) by 474 days.

This patent is subject to a terminal disclaimer.

(21) Appl. No.: 16/677,010

(22) Filed: Nov. 7, 2019

(65) Prior Publication Data

US 2020/0069428 A1 Mar. 5, 2020

Related U.S. Application Data

(63) Continuation of application No. 15/917,108, filed on Mar. 9, 2018, now Pat. No. 10,507,111.

(51) Int. Cl.
*A61F 2/30* (2006.01)
*A61F 2/50* (2006.01)
*B33Y 80/00* (2015.01)

(52) U.S. Cl.
CPC .............. *A61F 2/30* (2013.01); *A61F 2/5046* (2013.01); *A61F 2002/30079* (2013.01);
(Continued)

(58) Field of Classification Search
CPC .... A61F 2002/30079; A61F 2/30; A61F 2/32; A61F 2/34; A61F 2002/30316;
(Continued)

(56) References Cited

U.S. PATENT DOCUMENTS 4,024,588 A * 5/1977 Janssen ..................... A61F 2/30
623/18.12
5,507,835 A 4/1996 Jore
(Continued)

FOREIGN PATENT DOCUMENTS

| CN | 101940507 A | 1/2011 |
| WO | WO2008044229 | 4/2008 |
| WO | WO2008057565 | 5/2008 |

OTHER PUBLICATIONS

Ellen Jan Kleinerman, CWRU researcher developing test for prosthetic joint problems, http://www.cleveland.com/healthfit/index.ssf/2013/03/cwru_researcher_developing_tes.html, Mar. 18, 2013.
(Continued)

*Primary Examiner* — Alvin J Stewart
(74) *Attorney, Agent, or Firm* — Smith Tempel Blaha LLC; Matthew T. Hoots

(57) ABSTRACT

The present invention is directed generally to (1) an articulating junction, and articulation method thereof, wherein articulation is facilitated by a plurality of magnetic particles; (2) an articulating junction, and articulation method thereof, wherein the stability and fluidity of the junction is based, at least in part, on the magnetic field(s) of the plurality of magnetic particles; and (3) reducing the resistance to articulation and/or increasing the structural integrity and support, of the articulating junction, via electro-magnetism. Further, the present invention is directed generally to the synergistic combination of magnetic particles and preferred bio-implant-materials and additive-manufacturing methods along with Baker correlation codes. Further, the present invention is directed to an artificial joint for implantation into a living body and methods for constructing such an artificial joint.

8 Claims, 13 Drawing Sheets

(52) U.S. Cl.
CPC ........... *A61F 2002/3082* (2013.01); *A61F 2002/30108* (2013.01); *A61F 2002/30797* (2013.01); *A61F 2002/5047* (2013.01); *A61F 2210/009* (2013.01); *A61F 2220/0025* (2013.01); *A61F 2230/0063* (2013.01); *A61F 2310/00017* (2013.01); *A61F 2310/00023* (2013.01); *B33Y 80/00* (2014.12)

(58) Field of Classification Search
CPC .. A61F 2002/30317; A61F 2002/30668; A61F 2002/30685; A61F 2002/30052
See application file for complete search history.

(56) References Cited

U.S. PATENT DOCUMENTS

| | | | | |
|---|---|---|---|---|
| 6,599,321 | B2* | 7/2003 | Hyde, Jr. | A61B 17/68 623/18.12 |
| 6,764,520 | B2 | 7/2004 | Deffenbaugh et al. | |
| 7,101,374 | B2* | 9/2006 | Hyde, Jr. | A61B 17/68 606/60 |
| 7,811,328 | B2* | 10/2010 | Molz, IV | A61F 2/442 623/17.16 |
| 7,922,773 | B1 | 4/2011 | Kuiken | |
| 8,273,130 | B2* | 9/2012 | Gradl | A61F 2/30 623/18.12 |
| 8,287,594 | B2* | 10/2012 | Cragg | A61F 2/3872 623/14.12 |
| 8,465,453 | B2* | 6/2013 | Sandhu | A61L 27/28 604/96.01 |
| 8,845,741 | B2* | 9/2014 | Boyden | A61F 2/30 623/18.11 |
| 9,091,309 | B2* | 7/2015 | Battlogg | F16F 9/535 |
| 9,757,585 | B2* | 9/2017 | Bonutti | A61F 2/32 |
| 9,956,080 | B1* | 5/2018 | Howard | A61F 2/3094 |
| 10,507,111 | B2* | 12/2019 | Johnson | A61F 2/30 |
| 2002/0032484 | A1* | 3/2002 | Hyde, Jr. | A61F 2/40 623/18.12 |
| 2003/0005849 | A1* | 1/2003 | Post | B60L 13/04 104/2 |
| 2003/0153806 | A1 | 8/2003 | Miller | |
| 2005/0010300 | A1 | 1/2005 | Disilvestro | |
| 2005/0010301 | A1 | 1/2005 | Disilvestro | |
| 2006/0149386 | A1 | 7/2006 | Clarke | |
| 2006/0282168 | A1 | 12/2006 | Sherman | |
| 2007/0010702 | A1* | 1/2007 | Wang | A61F 2/82 600/8 |
| 2007/0088442 | A1* | 4/2007 | Cima | A61B 5/4528 623/18.11 |
| 2007/0100457 | A1* | 5/2007 | Hyde, Jr. | A61B 17/88 623/18.12 |
| 2007/0233251 | A1* | 10/2007 | Abdou | A61F 2/4405 623/17.11 |
| 2008/0306324 | A1* | 12/2008 | Bonutti | A61F 2/38 600/12 |
| 2010/0003649 | A1 | 1/2010 | Simon | |
| 2010/0036493 | A1* | 2/2010 | Simon | A61B 17/562 623/14.12 |
| 2010/0234954 | A1 | 9/2010 | Justis | |
| 2010/0331993 | A1* | 12/2010 | Gradl | A61F 2/30 623/23.4 |
| 2014/0086962 | A1 | 3/2014 | Jin | |
| 2014/0088721 | A1 | 3/2014 | Boyden | |
| 2015/0005886 | A1* | 1/2015 | Pinneo | A61F 2/32 623/18.12 |
| 2017/0029935 | A1 | 2/2017 | Li | |
| 2017/0224495 | A1* | 8/2017 | Rogachefsky | A61F 2/36 |
| 2018/0085459 | A1* | 3/2018 | Fahmy | A61N 2/06 |
| 2019/0167847 | A1* | 6/2019 | Park | A61K 35/32 |

OTHER PUBLICATIONS

TT Liao et al., Blomed Mat, Dose-dependent cytotoxicity evaluation of graphite nanoparticles for diamond-like carbon film application on artificial joints, http://iopscience.iop.org/article/10.1088/1748-605X/aa52ca/meta, Jan. 24, 2017.

Taylor et al., IJ NanoMed, The use of Superparamagnetic nanoparticles for prosthetic biofilm prevention, International Journal of Nanomedicine, https://www.ncbi.nlm.nih.gov/pmc/articles/PMC2747349/pdf/ijn-4-145.pdf, Aug. 11, 2009.

* cited by examiner

MAGNETIC PROSTHETIC

BACKGROUND OF THE INVENTION

Technical Field

The present invention is generally directed to an articulating junction, and articulation method thereof, wherein articulation is facilitated by a plurality of embedded magnetic granules/grains and, in one exemplary embodiment, a polymer bonded magnetic system(s). The present invention also is generally directed to an articulating junction, and articulation method thereof, wherein the stability and fluidity of the junction is based, at least in part, on the specific stray magnetic field(s), and the corresponding magnetization profile and structure-in-volume/bulk geometric shape, of the embedded magnetic profile. Further, the present invention is directed generally to: (1) reducing the resistance to articulation, and/or (2) increasing the structural integrity and support, of the articulating junction, via predefined stray magnetic field(s) (e.g., non-mechanical forces acting on at least a portion of the articulating junction based at least in part on a predefined variable magnetic pattern, shape, and/or fraction in the articulating junction).

Further, the present invention is generally directed to the synergistic combination of embedding magnetic patterns, shapes, and/or bulk geometric structures, via software-controlled magnetization processes, with preferred bio-implant-materials and additive-manufacturing methods. In this way, the present invention also is generally directed to methods, and therapeutic devices/implants/prosthetics, and methods of manufacture thereof, for the prevention and treatment of various conditions (e.g., amputations, replacements, augmentations, and secondary conditions like inflammation, auto-immune rejection, osteolysis).

Further, the present invention is directed to an artificial joint for implantation into a living body and methods for constructing such an artificial joint. In some embodiments, a magnetic prosthetic solution, that overcomes the above shortcomings in the prior art, leverages nano-magnetic structures or programmable magnets for in situ, in vivo use (e.g., under biological conditions and immunoactivity) that provides a smooth translation of the joint through its range of motion.

Prior Art

The stability and structural integrity of an articulating junction, in the field of biomechanics for example, is a compromise between biomechanics of design and integrity of existing biological structures.

Orthopedics is a medical subspecialty that treats disorders of the human body related to bones, muscles, ligaments, tendons, and joints, with its current emphasis on the treatment of the bones and joints. The treatment of bone and joint disorders can be generally sub classified into categories including the treatment of bone fractures, joint instability, early stage arthritis, and end stage arthritis. Originally, the treatment of orthopedic conditions mainly relied on casting and bracing. With the advent of new implantable materials, however, and development of better joint replacement prostheses, orthopedics shifted its focus to become increasingly more of a surgical subspecialty. With improved materials, better engineering, and a better understanding of the human body, the practice of orthopedic medicine and biomechanical experimentation have made remarkable progress. The treatment of bone fractures and joint disorders has continually been refined to the present state of the art.

Prior art innovations have concentrated on developing static mechanical design characteristics and new implantable materials used for fracture treatment in total joint arthroplasties. These static mechanical design characteristics have been directed to solutions for problems concerning wear, stability, and methods of fixation for the total joint arthroplasties. They have also been utilized to improve the current state of the art concerning fracture treatment.

Arthroplasty is a surgical procedure used to restore the function of a joint by resurfacing the bone with a prosthetic joint. In the case of both knee and hip arthroplasty, this procedure can help relieve pain and restore function in a severely diseased joint. This treatment option involves cutting away damaged bone and cartilage and replacing it with an artificial joint made of either metal alloys, high-grade plastics or polymers. This type of treatment procedure known in the art produces reliable symptomatic relief but are prone to instability and premature wear, especially in younger more active patients. Physiological impacts, such as tissue inflammation surrounding the prosthesis, often are the cause of premature artificial joint failure (described in greater detail below).

As a result, revision surgery for joint replacement failure may be necessary due to the corrosion or wear on the implant surfaces. Additionally, in terms of hip joint failure the most common problem is dislocation due to the fact that the man-made hip is smaller than the original joint, this causes the ball to come out of its socket.

More specifically, hip and knee joint replacements are the most commonly performed joint replacement surgical procedures in which parts of an arthritic or damaged joint is removed and replaced with a metal, plastic or ceramic device termed joint implants. Joint implants or what commonly can be referred as prosthetic joints, are long-term implantable surgical devices that are used to either completely or partially replace the structural elements within the musculoskeletal system to improve and enhance the function of the joint.

The basic anatomy of a joint is where the ends of two or more bones meet. Specifically, the knee joint is one of the largest and most complex joints in the body. The knee, also known as the tibiofemoral joint, is a synovial hinge joint formed between three bones: the femur, tibia, and patella. Further, the joint-forming surfaces of each bone are covered in a thin layer of hyaline cartilage that gives them an extremely smooth surface and protects the underlying bone from damage. Between the femur and tibia is a figure-eight-shaped layer of tough, rubbery fibrocartilage known as the meniscus. The meniscus acts as a shock absorber inside the knee to prevent the collision of the leg bones during strenuous activities such as running and jumping.

As mentioned, the knee is a type of synovial joint, as with all synovial joints, a joint capsule surrounds the bones of the knee to provide strength and lubrication. This capsule is composed of fibrous connective tissue continuous with the ligaments of the knee to hold the joint in proper alignment. Further, the anterior, posterior and medial surfaces of the knee are all held in place by various ligaments and these structures along with the joint capsule help support the knee by maintaining its ability to permit the flexion and extension of the lower leg relative to the thigh.

Physiology changes to the above mentioned joint structures are thought to contribute towards the progression of a diseased knee joint leading to the consideration of joint replacement surgery. Some of these changes includes: measureable differences in overall knee cartilage volume and tibial cartilage volume, measurable differences in bone size, meniscal tears and bone marrow lesions.

The hip joint is also a type of synovial joint, specifically termed a ball- and socket synovial joint. The ball is the femoral head and the socket is the acetabulum. The femur is the longest and heaviest bone in the human body and consist of a superior/proximal end, a shaft, and an inferior/distal end. It is the superior end of the bone connecting to the side of the acetabulum. The superior end of the femur consists of a head and a neck, to which the head of the femur is angled superomedially and slightly anteriorly when connecting with the acetabulum. The head is attached to the femoral body (shaft) by the neck of the femur.

The hip joint is the articulation of the pelvis with the femur, which connects the axial skeleton with the lower extremity. The hipbone is formed by the fusion of the ilium, the ischium, and pubis. The ilium is the largest part of the hip bone and makes up the superior part of the acetabulum. The ischium is the inferior aspect of the pelvis, the superior part of the ischium fuses with the pubis and ilium, forming the posteroinferior aspect of the acetabulum. The pubis, makes up the anteromedial part of the hip bone and contributes to the anterior part of the acetabulum. As noted, the acetabulum is formed from parts of the ilium, ischium, and pubis. This a cup-shaped socket component on the lateral aspect of the pelvis which articulates with the head of the femur to form the hip joint.

The hip joint can be defined as the connection of the proximal side of the acetabulum and the distal neck portion of the femur by strong fibrous capsules and ligaments. As in the knee joint, physiology changes to these structures are thought to contribute towards the progression of decreased function and pain in the hip joint leading to the consideration of joint replacement surgery. Some of these changes include: measureable differences in overall cartilage volume and measureable changes in bone mineral density.

Artificial joint prostheses are used as a surgical therapeutic substitute for joint components that are damaged, such as due to injury or osteoarthritis. The goals of surgical implantation of artificial joint prostheses generally include improving joint function and alleviating pain. Although these surgeries have a high success rate, there is some risk over time that an artificial joint prosthesis can fail. Failure of artificial prosthetic joints can require further surgery, with associated costs and morbidity for the patient. One clinically significant type of artificial joint failure is associated with loosening of the prosthesis at the bone interface, including osteolysis and related damage to the bone.

Artificial joint prosthesis failure is associated in a significant number of cases with loosening of the prosthesis at the prosthesis-joint interface or in the periprosthetic region due to loss of the adjacent bone. This is believed to be caused in part from osteolysis promoted by the body's response to debris from the artificial joint prosthesis. Wear debris from the prosthesis surface coming into contact with the bone-prosthesis interface has been implicated, for example, in loosening of the prosthesis and associated failure. Debris particles at the prosthesis-bone interface can contribute to osteolysis and resulting prosthesis loosening with potential failure of the prosthesis.

Debris particles within the synovial fluid can include, for example, one or more of: cellular debris particles, particulates of bone and prosthesis generated during surgery, and particulates formed from wear of the artificial joint prosthesis. Some studies indicate that debris particles can enter the prosthesis-bone interface region through increased synovial fluid pressure at the prosthesis-joint interface during physiological movement. Some studies indicate that debris particles can enter the prosthesis-bone interface region through increased synovial fluid flow rate against the prosthesis joint interface during physiological movement. Studies also indicate that both fluid pressure and flow rate at the prosthesis-joint interface due to prosthesis movement during physiological activities encourage debris particles to enter the prosthesis-bone interface, contributing to osteolysis and prosthesis failure.

To combat such failures in the prior art, prior art solutions have incorporated discrete conventional standard magnet inserts or plugs at the juxtaposed surfaces of a prosthesis in an effort to leverage magnetically repelling forces to reduce friction. Prior art solutions using a plurality of discrete and embedded magnets in prosthesis, however, have exhibited undesirable performance characteristics. For example, prior art solutions that embeds magnets in a prosthetic joint are prone to corrosion. Additionally, patients using prior art solutions that embed magnets in a prosthetic joint tend to experience a "jerky" motion as the various embedded magnets sequentially release from, and subsequently engage, complementary magnetic fields generated by other nearby embedded conventional standards magnets.

Pursuant to the foregoing, it may be regarded as an object of the present invention to overcome the deficiencies of, and provide for improvements in, the state of the prior art as described above, and as may be inherent in the same, or as may be known to those skilled in the art. It is a further object of the present invention to provide a therapeutic treatment and method and any necessary apparatus for carrying out the same, and of the foregoing character, and in accordance with the above objects, which may be readily carried out, with and within the process, and with comparatively simple equipment, and with relatively simple engineering requirements. Still further objects may be recognized and become apparent upon consideration of the following specification, taken as a whole, wherein by way of illustration and example, an embodiment of the present invention is disclosed.

As used herein, any reference to an object of the present invention should be understood to refer to solutions and advantages of the present invention, which flow from its conception and reduction to practice, and not to any a priori or prior art conception.

The above and other objects of the present invention are realized and some limitations of the prior art are overcome in the present invention by providing new and improved methods, processes, compositions, and systems. A better understanding of the principles and details of the present invention will be evident from the following description.

BRIEF SUMMARY OF THE INVENTION

An exemplary embodiment of the present invention relates to prosthetic components and, in particular, to total joint replacement using embedded magnetic granules/grains to control the instability of joint-replacement surgery.

The exemplary embodiment may comprise embedded magnetic granules/grains that may be manipulated, using magnetic fields, to obtain specifically and purposely designed magnetic system(s). Further, the exemplary embodiment may comprise magnetic filler particles (for example, soft magnetic alloys or hard magnetic alloys like ferrite as well as rare-earth materials—embedded inside a thermosoftening polymer binder matrix to form a polymer bonded permanent magnet with the freedom of having a specific complex shape with locally tailored magnetic properties and predefined stray field(s) in a given region. The prosthetic component also may comprise conductive graphene/PLA composite filament and/or ceramics or electromagnets.

Further, the exemplary embodiment may comprise locally-different polymer-matrix material concentrations, and different types of magnetic filler particles, as well as continuous changes from magnetic material to non-magnetic material. This provides tailored magnetic properties and/or smooth transitions between strong and weak magnetism, offering applications requiring custom external field profiles.

The polymer bonded permanent magnet may be isotropic (non-directional) or anisotropic (directional) with high dimensional accuracy. If anisotropic, the magnetic system may be produced, at least in part, via a software controlled magnetization process that locally magnetizes or aligns the magnetic particles during the solidification/formation process. This enables precision control over the magnetic field(s).

The exemplary embodiment also may comprise a magnetic structure that incorporates correlated patterns of magnets with alternating polarity, designed to achieve a desired behavior and deliver strong localized magnetic fields. The prosthetic component (or repaired articulation junction, etc.) comprising the magnetic structure may be configured as a multipole structures made up of multiple magnetic elements (maxels) of varying size, location, orientation, and saturation. By accurately arranging or overlapping the maxels, for example, and by varying the polarity and/or field strengths of each source of the arrays of magnetic sources that make up the magnetic structure, intricate magnetic fields or stray fields are produced, and may be leveraged to control the instability of joint-replacement surgery.

The exemplary embodiment also may comprise magnetic nano-particles to control the instability of joint-replacement surgery; however, the nano-scale is merely a non-limiting example.

Further, an exemplary embodiment of the present invention provides a prosthetic system that incorporates embedded magnetic granules/grains, a magnetic pattern, shape, and/or bulk geometric structure, or nano-magnetic particles, or programmable magnets, etc. into either the fabrication of the various prosthetic components, or onto the surfaces of the various prosthetic components, or directly into the articulating junction to be repaired. The fabrication process of the magnetic system may involve encapsulation/surrounding of the magnetic elements or particles of the magnetic system with a biocompatible shell/buffer such as silica or graphene.

If primarily magnetic particles, for example, either nano- or micro etc., the fabrication process may further be processed by either: (1) Dispersion of the encapsulated magnetic particles in a solution of either methyl methacrylate (PMNIA), polyethylene(PE), and/or a biocompatible oxide ceramic and allow the magnetized material to harden into a solid state to construct the prosthetic with the use of 3D printing; (2) Application of the magnetic particle solution such that it is adhered to surfaces of the prosthetic joint (such as via a structured film comprised of layers of liquid or dried powder comprising the encapsulated magnetic nanoparticles); and/or (3) Collection of magnetic particles in a dried powder such that it is manufactured into an alloy for the creation of an oxygen-diffused outer surface of the joint prosthetic. Spraying a jet of materials and/or magnetic particles onto the surface/structure being built up may be involved as a method step as well.

Further, an exemplary embodiment of the present invention provides a solution that leverages the embedded magnetic granules/grains, the magnetic pattern, shape, and/or bulk geometric structure, or nano-magnetic particles, or programmable magnets, etc. to create a low friction "cushion" between two surfaces of a prosthetic joint. It is also envisioned that other embodiments of the solution may leverage the embedded magnetic granules/grains, the magnetic pattern, shape, and/or bulk geometric structure, or nano-magnetic particles, or programmable magnets, etc. to generate an attractive force between two surfaces in a prosthetic joint, thereby mitigating the probability of joint separation. It is possible that a spring-like effect may be created and leveraged as well.

Further, an exemplary embodiment of the present invention provides a solution that uses of rare-earth, magnetic-field joint surfaces in the prosthetic components, as opposed to prior art solutions that simply embed a plurality of conventional standard magnet plugs, and, in doing so, may overcome the prior art shortcomings.

Further, an exemplary embodiment of the present invention provides a prosthetic system comprising a magnetic system configured to yield a specific pre-determined stray magnetic field of complex form. The stray field may be configured as a special magnetic field with field lines arranged in a very specific way—such as a magnetic field that remains relatively constant along one direction but which varies in strength along another direction, as a non-limiting example. In one exemplary embodiment, in order to achieve such requirements, the magnetic system, if produced via additive manufacturing methods, is produced with a sophisticated geometric form.

The magnetic system may be designed via computer software, before or during, which adjusts the shape until all requirements for the desired magnetic profile are met. Once the desired geometric shape, the additive manufacturing system may use specialty produced filaments of a magnetic particle, which are held together by a polymer binding material preferred for prosthetics. The additive manufacturing system may prepare the additive material for application and may apply it point-by-point in the desired locations using a nozzle or spray or atomizer or particle deflector or accelerator. This results in a customized, made-to-order, on-demand system that is cost- and time-effective, which can be customized and adjusted before or during manufacture.

Further, an exemplary embodiment of the present invention provides a prosthetic system comprising a magnetic system configured to yield a specific pre-determined stray magnetic field, but which requires a software-controlled magnetization process to adjust the orientation and/or polarity of the magnetic system (before or during manufacture). The software-controlled magnetization process enables precision control over the magnetic field of the final product. In this way, the magnetic system may provide improved attraction forces, repulsion forces, and/or alignment, which is impossible with conventional standard magnet plugs or plates. In one exemplary embodiment, the software-controlled magnetization process applies, at least in part, Barker correlation codes, from communications theory, to the magnetic system.

For example, the magnetic system may be designed to not only hold when attached but, unlike a convention magnet, it may be engineered with a distinct and separate force curve to also lightly repel when misaligned or aligned or partially aligned, etc. Further, the magnetic system may lightly repel anywhere along its length/shape/pattern when not aligned/ aligned and may precisely align and attract with substantial strength when oriented appropriately. In the end, the magnetic system may operate at least in part as a polymagnetic spring and/or polymagnetic latch and/or equivalent as is understood in the art. It is envisioned that the software-controlled magnetization process may involve locally magnetizing, or aligning, magnetic particles if applicable during the solidification process to obtain complex internal magnetization profiles.

Further, an exemplary embodiment of the present invention provides a prosthetic system that incorporates magnetic nano-particles with biocompatible shells, respectively, comprising alloys of rare-earth elements including: lanthanide, scandium and yttrium. The magnetic nano-particle-imbued solution essentially comprises an exchange-coupled nano-composite architecture wherein the atoms of rare-earth elements have high magnetic momentum or torque.

Further, an exemplary embodiment of the present invention provides an exemplary embodiment of a prosthetic joint comprising correlated magnet pairs programmed to attract and/or repel with a prescribed force and engagement distance, or to attract and/or repel at a certain spatial orientation. The correlated magnets may be engineered to interact only with other magnetic structures that have been similarly engineered to respond, for example, with others that yield a cog-shaped field. The correlated magnets also may have a resulting magnetic structure that is one-dimensional, two-dimensional, three-dimensional, if produced using an electromagnetic array; however, multipole magnetic systems may be constructed from discrete permanent magnets, or by exposing heated magnetizable material, for example, to a coded magnetic field.

Further, an exemplary embodiment of the present invention provides an exemplary embodiment of a prosthetic joint comprising at least one component fabricated from at least one polymer and a plurality of magnetic particles. The at least one component fabricated from at least one polymer and a plurality of magnetic particles includes a surface subject to wear during physiological use of the joint, which can be described as a contact surface or a weight-bearing surface, for example.

Further, an exemplary embodiment of the present invention relates to a method of making a magnetized medical implant. The exemplary method includes the steps of providing a substrate and depositing a magnet particle layer onto a surface of the substrate and/or within a new or additional layer onto a substrate or base.

An exemplary magnetic prosthetic joint comprises at least one component that includes at least a first plurality of magnets configured to create a magnetic field within, about, and/or surrounding the joint, the magnetic field directed to influence the articulation and smooth and sturdy translation of the joint through its ranges of motion in vivo. The components of the prosthetic joint, therefore, may be influenced by the magnetic force while in their mechanical arrangement in vivo.

Embodiments of the nano-magnetic prosthetic according to the solution are not limited to the exemplary aspects and features described above or below. Certain embodiments may include additional features, or different features, while other embodiments include alternative features.

BRIEF DESCRIPTION OF THE DRAWINGS

In the Figures, like reference numerals refer to like parts throughout the various views unless otherwise indicated. For reference numerals with letter character designations such as "102A" or "102B", the letter character designations may differentiate two like parts or elements present in the same Figure. Letter character designations for reference numerals may be omitted when it is intended that a reference numeral to encompass all parts having the same reference numeral in all Figures.

DETAILED DESCRIPTION OF PREFERRED EMBODIMENTS

Figure 1B:
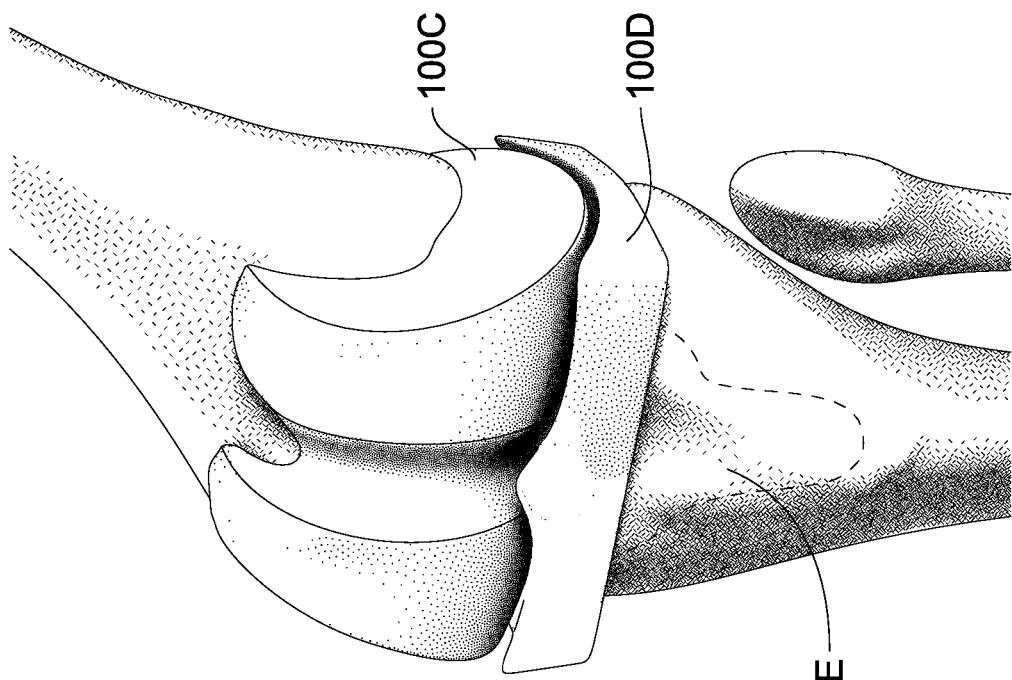
FIGS. 1A and 1B collectively illustrate an exemplary embodiment of a prior art basic artificial knee joint structure showing a diseased knee replaced by an artificial joint made of either metal alloys, high grade plastics or polymers, in which a plastic spacer in placed between the femoral and tibial component.

For a further understanding of the nature, function, and objects of the present invention, reference should now be made to the following detailed description. While detailed descriptions of the preferred embodiments are provided herein, as well as the best mode of carrying out and employing the present invention, it is to be understood that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure, or manner.

The present invention is based, at least in part, on the discovery that the electro-magnetic fields of embedded magnetic granules/grains, magnetic patterns, shapes, and/or bulk geometric structures, or nano-magnetic particles, or programmable magnets, etc., and the attractive and/or repulsive forces correlated thereto, can be leveraged to improve the structure and operation of an articulating junction.

As context, there have been some prior art attempts to develop applications that utilize nonmechanical forces to augment the treatment of particular orthopedic problems. For example, a pulsating electromagnetic field has been used as an adjunct to stimulate bone healing. Biochemical and biomaterial means have been used to alter the environment at fracture sites and in joints to aid healing and to decelerate disease processes. Others have attempted to utilize magnetic fields in treatment of bone and joint disorders as well.

By using a nonmechanical force, such as magnetized implants, to supplement a joint, various wear problems may be eliminated from the joint implant. Wear problems are often caused by excessive articulation between two elements and often result in additional surgeries to a patient to replace worn implants. Since two elements having a resultant repulsive magnetized force do not generally abut one another, the wear between two such elements is greatly reduced, thereby extending the life expectancy of the implant. There remains a need in the art, however, for improved devices and methods for restraining bones in treatment of orthopedic conditions using implants with embedded magnetic systems.

For example, conventional magnets are mainly produced by sintering (using heat, pressure, or both, to create a solid from a mass of powder, for example, and then cutting and/or slicing and/or chiseling into the required shape) or injection molding and hence limited in complexity of their shapes. For sintering, manufacturing may result in material waste of as much as 30% to 50% of the original material as the sintered product is more brittle and prone to corrosion. For injection molding, including magnetic elements into the mold substrate requires particular and limited fluidity requirements. This is due to rising filler content which increases the viscosity of the compound, leading to filling problems within the mold cavity. For this reason, the matrix material is limited to being those of high flowablility and good mechanical properties. In either situation, standard magnets are limited to a basic, conventional field based on the standard north south polarity alignment. Further, the field is not inherently limited in terms of field strength, distance, or interference. In this way, it must be kept in mind throughout this disclosure that you cannot change the shape of the force curve on a conventional magnet, nor define how it behaves when misaligned/properly aligned. These are all but some of the limitations of the prior art.

Herein, the unexpected role of embedded magnetic granules/grains, magnetic patterns, shapes, and/or bulk geometric structures, or nano-magnetic particles, or programmable magnets, etc., and derivatives thereof, as an articulating junction improvement, is explored.

At a very high level, an exemplary embodiment of the present invention relates to prosthetic components and, in particular, to total joint replacement using magnetic nano-particles to control the instability of joint-replacement surgery. Further, the exemplary embodiment may comprise magnetic nano-particles that may be manipulated using magnetic fields. The physical and chemical properties of these magnetic nano-particles may largely depend on their synthesis method and chemical structure.

As is understood by a person having ordinary skill in the art, magnetic nano-particles may range from 1.0 to 100.0 nm in size. Further, individual nano-particles when clustered together may form nanospheres which can be assembled into a material that is agglomerated, highly concentrated and deliverable in a solution or as a dried powder suitable for dispersion in water or other solvent. Specifically, it is envisioned that magnetic iron oxide nanoparticles that can be produced via the thermal decomposition of organometallic precursors at high temperature in organic solvent, producing highly monodisperse, organic-solvent compatible nanoparticles, may be transferred into aqueous-compatible solvents by modifying the surface of the nanoparticles or growing a uniform silica coating around nanoparticles.

Further, the magnetic nano-particles comprised within the exemplary embodiment may comprise magnetic material including iron, nickel, cobalt, etc.; however, it is envisioned that a magnetic nano-particle material may be colloidal iron oxide($Fe_3O_4$), which is known to exhibit superparamagnetic properties at ambient temperatures and, as such, may be preferred for biomedical applications. The size, non-toxicity and superparamagnetic properties of magnetic nano-particles make them preferred for fabrication of prosthetic joints, for example.

Further, and with reference to structure and methods of manufacture or use, an exemplary embodiment of the present invention provides a prosthetic system that incorporates magnetic nano-particles into either the fabrication of the various prosthetic components or onto the surfaces of the various prosthetic components. The fabrication process may involve encapsulation of iron-core magnetic nano-particles with a biocompatible shell (to combat corrosion, and immunological responses, and prevent toxic leaching, for example) such as silica or graphene. The fabrication process may then further be processed by either: (1) Dispersion of the encapsulated magnetic nano-particles in a solution of either methyl methacrylate (PMMA), polyethylene(PE), and/or a biocompatible oxide ceramic and allow the magnetized material to harden into a solid state to construct the prosthetic with the use of 3D printing; (2) Application of the magnetic nano-particle solution such that it is adhered to surfaces of the prosthetic joint (such as via a nano-structured film comprised of layers of liquid or dried powder comprising the encapsulated magnetic nanoparticles); and/or (3) Collection of magnetic nano-particles in a dried powder such that it is manufactured into an alloy for the creation of an oxygen-diffused outer surface of the joint prosthetic.

Further, an exemplary embodiment of the present invention provides a solution that uses encapsulated magnetic nano-particle to create a low friction "cushion" between two surfaces of a prosthetic joint (such as in a knee). It is also envisioned that other embodiments of the solution may use encapsulated magnetic nano-particles to generate an attractive force between two surfaces in a prosthetic joint, thereby mitigating the probability of joint separation (such as in a shoulder).

Further, an exemplary embodiment of the present invention provides a solution that uses of rare-earth, magnetic-field joint surfaces in the prosthetic components, as opposed to prior art solutions that simply embed a plurality of standard magnetic plugs, and, in doing so, may overcome the prior art shortcomings. Benefits of the solution include, but are not limited to, unaltered joint space, no third body wear, decrease in osteolysis, and minimal bone stock loss.

Further, an exemplary embodiment of the present invention provides a prosthetic system that incorporates magnetic nano-particles with biocompatible shells, respectively, comprising alloys of rare-earth elements including: lanthanide, scandium and yttrium. The magnetic nano-particle-imbued solution essentially comprises a exchange-coupled nano-composite architecture wherein the atoms of rare-earth elements have high magnetic momentum or torque. The exchange-coupled nanocomposite may be fabricated utilizing nanoparticles as building blocks, by exploiting nanoscale effects, and, therefore, facilitates the production of permanent magnet/magnetic features. Similarly, the nanocomposites may be composed of soft magnetic alloys or hard magnetic alloys like ferrite—e.g., Sr. Ba—as well as rare-earth materials—e.g., neodymium ion boron [NdFeB] or samarium cobalt [SmCo] or dysprosium that are ideal for generating a permanent magnet.

Further, an exemplary embodiment of the present invention provides an exemplary embodiment of a prosthetic joint comprising at least one component fabricated from at least one polymer and a plurality of magnetic particles. The at least one component fabricated from at least one polymer and a plurality of magnetic particles includes a surface subject to wear during physiological use of the joint, which can be described as a contact surface or a weight-bearing surface, for example. The magnetic particles within the polymer may be dispersed within the polymer structure or within a layer/portion/frequency of the structure at a density sufficient and satisfactory to known and expected safety standards in the biomedical field.

Further, an exemplary embodiment of the present invention provides an exemplary embodiment of a prosthetic joint comprising at least one component fabricated from at least one polymer and a plurality of magnetic particles, wherein the magnetic particles are derived from filament containing 45-65% by volume of magnetic granules. As the filament is melted, it is extruded by the printer, for example, to build a shape up layer-by-layer. It is envisioned that the magnetic granules start out in an unmagnetized state, but placing the printed object into a strong magnetic field of the required geometry (described in greater detail herein) converts them into the desired magnetic profile, which can then be retained permanently.

As a non-limiting alternative, the process may start with pellets containing a blend of 65% NdFeB and 35% nylon, for example. The NdFeB particles/granules may be initially demagnetized; each particle having approximately zero net magnetization. These components may then be melted and extruded by a system like the Big Area Additive Manufacturing (BAAM) machine. In another alternative, the process is intended for a lower-cost, end-user commercially available 3D printer (such as the Builder 3D printer from Code P®) with commercially available NdFeB powder inside a PA11 or PA12 matrix. In another alternative, the process may start with magnetically isotropic powder, which is preferred because it comes with lower assembly costs and more flexibility. In another alternative, the process may start with prefabricated compound (Neofer® 25/60p) from Magnetfabrik Bonn GmbH, for example.

Further, an exemplary embodiment of the present invention relates to a method of making a magnetized medical implant. The exemplary method includes the steps of providing a substrate and depositing a magnet nano-particle layer onto a surface of the substrate and/or within a new or additional layer onto a substrate or base. The method may include magnetizing the magnetizable layer by exposing it to a magnetic field, as well as depositing a corrosion resistant layer onto the magnetizable layer. The method may further include depositing a wear resistant layer onto the corrosion resistant layer. The corrosion and wear resistant layers may be deposited using a process selected from the group consisting of chemical vapor deposition, physical vapor deposition, sputtering, and plating.

An exemplary nano-magnetic prosthetic joint comprises at least one component that includes at least a first plurality of nano-magnets configured to create a magnetic field within, about, and/or surrounding the joint, the magnetic field directed to influence the articulation and smooth and sturdy translation of the joint through its ranges of motion in vivo. The components of the prosthetic joint, therefore, may be influenced by the magnetic force (a non-mechanical force, for example) while in their mechanical arrangement in vivo. In this way, the reduction of resistance to articulation, and/or the augmentation of the structural integrity and support, of the articulating junction, via electro-magnetism, in vivo reduces the possibility of osteolysis at the bone interface, which in turn may reduce the incidence of prosthesis failure. In addition, any debris particles that include physiological components, such as antibodies or macrophages, for example, will also include the nano-magnetic particles and may be influenced by internal/external magnetic field(s).

Further, an exemplary nano-magnetic prosthetic joint may be suitable for: a hip joint prosthesis, a knee joint prosthesis, a shoulder joint prosthesis, an ankle joint prosthesis, or an elbow joint prosthesis, etc. Although the artificial joint prostheses are described herein primarily in reference to humans, in some embodiments the artificial joint prostheses as described herein will also have applicability in veterinary medicine.

Further, an exemplary nano-magnetic prosthetic joint comprises at least one component with a bone-facing surface of the artificial joint prosthesis, the bone-facing surface configured to face a bone-prosthesis interface in vivo. For example, the bone-facing surface of a component of the artificial joint may include: a region of a shell of a acetabular component of a hip joint prosthesis; a region of a liner of a acetabular component of a hip joint prosthesis; a region of a stem of a femoral component of a hip joint prosthesis; a region of a femoral component of a knee joint prosthesis; a region of a tibial component of a knee joint prosthesis; a region of a humeral stem of a shoulder joint prosthesis; a region of a humeral component of a shoulder joint prosthesis; or a region of a glenoid component to a scapula of a shoulder joint prosthesis.

Further, an exemplary nano-magnetic prosthetic joint comprises at least one component with a contact surface, wherein the component is fabricated from at least one polymer integrating a plurality of magnetic particles. For example, in some embodiments, the component is fabricated from at least one polymer integrating a plurality of magnetic particles can include: an acetabular component of a hip joint prosthesis; a head of a femoral component of a hip joint prosthesis; a femoral component of a knee joint prosthesis; a tibial component of a knee joint prosthesis; a patellar component of a knee joint prosthesis; a humeral component of a shoulder joint prosthesis; or a glenoid component to a scapula of a shoulder joint prosthesis. In some embodiments, the component is fabricated from a polymer including the plurality of nano-magnetic particles embedded in a polymer matrix. In some embodiments, the component is fabricated from polyethylene including the plurality of magnetic particles embedded in a polymer matrix.

In some embodiments, the component is fabricated from at least one magnetic, polymer nano-composite material. In some embodiments, the plurality of magnetic particles include magnetic nanoparticles, which are magnetic particles sized between approximately 100.0 nanometers (nm) in diameter and approximately 1.0 nanometer (nm) in diameter. In some embodiments, the component is fabricated from a polymer including a plurality of magnetic nanoparticles at an average density no less than 10.0 magnetic nanoparticles per square micron ($\mu m^2$) of the polymer. In some embodiments, the component is fabricated from a polymer including a plurality of magnetic nanoparticles at an average density no less than 100.0 magnetic nanoparticles per square micron ($\mu m^2$) of the polymer. In some embodiments, the plurality of magnetic particles includes ferromagnetic particles. In some embodiments, the plurality of magnetic particles includes paramagnetic particles. The polymer integrating a plurality of magnetic particles may include polyethylene magnetic particles.

In some embodiments, the polymer integrating a plurality of magnetic particles may include polyethylene magnetic nanoparticles. The magnetic particles may be integrated into a polymer during fabrication of the artificial joint component. The polymer integrating a plurality of magnetic particles may include ultra-high-molecular weight polyethylene (UHMWPE). The polymer integrating a plurality of magnetic particles may include highly cross-linked UHMWPE.

The "contact surface" of an exemplary nano-magnetic prosthetic joint, as used herein, refers to a surface of a component that is expected to come into contact with another component of the joint during normal physiological use of the artificial joint in vivo. For example, a contact surface may include a joint-facing surface of an acetabular liner of a hip joint, a joint-facing surface of a head of a femoral component of a knee joint, or a joint facing surface of a glenoid component to a scapula of a shoulder joint prosthesis. A component including a load-bearing surface is a structural component of the artificial joint during expected physiological use of the joint. As used herein, a "non-contact surface" of an artificial joint prosthesis refers to a surface of a component of the artificial joint prosthesis that is expected to not come into contact with the bone and also to not come into contact with a surface of another component of the artificial joint prosthesis during normal physiological use of the artificial joint prosthesis in vivo. In some instances, a contact surface of an artificial joint may be a "load bearing surface," or a surface of a joint component that is expected to come into contact with another component and to partially support the mass of the individual user during normal physiological use of the artificial joint in vivo. A component including a load-bearing surface is a structural component of the artificial joint during expected physiological use of the joint in vivo.

In some embodiments, a contact surface of an artificial joint component includes one or more indentations at the contact surface. These indentations can be formed as lines, channels or patterns at the contact surface. A contact surface of an artificial joint component may include, for example, one or more grooves in the contact surface. The indentations or grooves in the contact surface are configured to provide a space for any limited wear debris from the artificial joint to accumulate away from a direct contact area of the contact surface.

In some embodiments, the artificial joint components include at least one component configured to magnetically shield the component including at least one magnet. The shielding component can, for example, be configured to minimize the magnetic field's influence beyond the immediate joint region.

Some embodiments include at least one fluid deflecting structure attached to a non-contact surface of the artificial joint. One or more fluid deflecting structures can, for example, be configured to operate synergistically with the magnetic field. Fluid deflecting structures can be configured, for example, as a flange or cuff-like structure attached to a non-contact surface of the artificial joint. Fluid deflecting structures can be configured, for example, as a plurality of ciliated projections. The fluid deflecting structures may be configured to divert synovial fluid flow away from the prosthesis-bone interface during physiological activity, and towards a desired location, such as in accord with the magnetic field(s) for example. The synovial fluid deflecting structures of the artificial joint prosthesis also may be configured to decrease the transient synovial fluid pressure at the prosthesis-bone interface during physiological activities.

The reduction of synovial fluid flow as well as transient pressure at the bone-prosthesis interface may lead to a reduction of any limited debris particles that may enter the prosthesis-bone interface during physiological movement. This may decrease the risk of osteolysis related to wear debris particles at the prosthesis-bone interface, thereby reducing the risk of prosthesis failure and the need for revision surgery with its associated costs and morbidity. In some embodiments, the prosthesis structures can include additional chemical inhibitors of osteolysis.

Returning to exemplary embodiments of a nano-magnetic prosthetic joint, one embodiment relates to a prosthetic bearing component for use in a joint replacement. The component may include a first element having a first magnetic nano-particle layer disposed thereon. There also may be a second element having a second magnetic nano-particle layer disposed thereon. The second element may be configured to engage the first element. The prosthetic bearing component may comprise a corrosion resistant layer covering the surfaces of the first and second elements about the first and second magnetized layers. Further, the component also may include a wear resistant layer covering the surfaces of the first and second elements adjacent the corrosion resistant layer and forming a bearing surface of the prosthetic bearing component.

Further, in an exemplary embodiment of a bearing surface of the prosthetic bearing component, the corrosion resistant layer is composed of a material selected from the group consisting of titanium, niobium, chromium, zirconium, tantalum, gold, silver, titanium nitride, titanium aluminum nitride, titanium carbonitride, chromium nitride, chromium carbonitride, zirconium nitride, and zirconium carbonitride, etc. The corrosion resistant layer may be configured as a film with a thickness of 0.1-50 microns. The exemplary embodiment of a bearing surface also comprises a wear resistant layer composed of a material selected from the group consisting of chromium oxide, aluminum oxide, chromium carbide, zirconium oxide, polyurethane, artificial cartilage, and ultra high molecular weight polyethylene. The wear resistant layer also may be a film with a thickness of 50.0-1000.0 microns. The corrosion resistant layer may be a film with a thickness of 0.1-5.0 microns. It should be noted that there are various options proven at industrial scale for producing titanium, tantalum, and various other metals and innovative alloy powders for the additive manufacturing market.

Returning to exemplary embodiments of a nano-magnetic prosthetic joint, one embodiment may comprise embedded iron oxide-based magnetic nano-particles in ultra-hard, molecular-weight polyethylene. The nano-particles are embedded without altering the chemical or structural properties of the hard plastic. Too many nano-particles weaken the properties of the plastic. Further, the polyethylene is an incredibly strong material, more scratch-resistant than carbon steel; however, its weakness, even in the inventive concept, is that chemical oxidation degrades the plastic.

As such, the exemplary embodiment takes into consideration and expects that each fragment of the polymer formed from wear during physiological use of the joint will include at least one of the magnetic nano-particles. The polymer fragments, therefore, are expected to have magnetic properties as a consequence of the inclusion of the magnetic nano-particles within the polymer structure.

It is envisioned that magnetic field may be directed to influence a location of debris including the magnetic particles in the joint to a position distinct from the bone-prosthesis interface in vivo. The fragments, therefore, of the polymer may be influenced by the magnetic field to a location within the joint that is distinct from the bone-prosthesis interface in vivo. The minimization of wear particle debris at the bone-prosthesis interface in vivo may reduce the possibility of osteolysis at the bone interface, reducing the incidence of prosthesis failure. In addition, any debris particles that include physiological components, such as antibodies or macrophages, will also include the magnetic particles and be influenced by the magnetic field. For example, a macrophage that has engulfed any fragments including magnetic particles would be influenced by the magnetic field within the joint.

Further, the exemplary artificial joint can include a second component of the artificial joint prosthesis including at least one magnet configured to create a magnetic field within the artificial joint, the at least one magnet positioned to form a magnetic field directed to influence a location of debris including the magnetic particles in the joint to a position distinct from the bone-prosthesis interface in vivo, wherein the location is within the indentations or grooves in the contact surface.

Further, the exemplary artificial joint can be used in conjunction with an external magnetic field. For example, the artificial joint may be used with an external magnetic field to enhance or promote the movement of wear fragments including the magnetic nano-particles to a particular location within the joint. For example, an external magnetic field may be applied periodically with the external magnetic field configured to provide greater magnetic field strength to the existing field of the joint. The external field can operate additively or synergistically, for example, with the internal field of the joint. The artificial joint also may be used in conjunction with an external magnetic field to determine the present, approximate number, concentration, and size of wear fragments including magnetic particles.

Further, and again at a very high level, an exemplary embodiment of the present invention provides a prosthetic system comprising a magnetic system configured to yield a specific pre-determined stray magnetic field of complex form. The stray field may be configured as a special magnetic field. In one exemplary embodiment, in order to achieve such requirements, the magnetic system comprises magnetic patterns, shapes, and/or bulk geometric structures, programmable magnets, and/or equivalents, manufactured at least in part via software-controlled magnetization processes. Additive manufacturing of the prosthetic system may be involved; however, it is envisioned that similar principles may be applied without having to create a bonded magnet.

Further, the magnetic system may be designed via computer software, before or during, which adjusts the shape until all requirements for the desired magnetic profile are met. In one exemplary embodiment involving additive manufacturing, once the desired geometric shape and magnetic profile is computed, the additive manufacturing system may use specialty produced filament(s) of a magnetic particle held together by a polymer binding material. The additive manufacturing system may prepare the additive material(s) for application and may apply it/them point-by-point in the desired locations with a variable magnetic compound fraction distribution. This means that saturation magnetization can be adjusted during the printing process to obtain the desired external field via, at least in part, a variable magnetic compound fraction. The result may be a prosthetic system comprising a component or portion or region or gradient composed of roughly between 70-90% magnetic material and 30-10% substrate in some regions, and also roughly between 40-65 vol. % magnetic material in other regions. This results in a customized, made-to-order, on-demand system that is cost- and time-effective, which can be customized and adjusted before or during manufacture.

In another exemplary embodiment, a twin-screw mixing extruder is used to mix magnetic filaments/source material with bio-prosthetic preferred substrate material/filaments. The magnetic source material and the substrate material are compounded, extruded, and characterized or prepared to be characterized for the printing process. It is envisioned that the printing process is carried out directly from formless (liquid, powders, etc.) or form-neutral (tape, wire) material, mostly be means of thermal or chemical processes. No specific tools or methods are required; however, fused deposition modeling technology may be employed for this embodiment. It is envisioned that the magnetic particles may be initially produced by a melt spinning process (described in greater detail herein), wherein ribbons or flakes with a size about 200 microns is produced (inert gas atomization processes are also envisioned to produce spherical particulates of approximately 45 microns; other process yield spherical particles having a diameter of approximately 50+/−20 microns). Further, it is envisioned that the mixing extruders can continuously change between materials of different concentrations and/or compositions, and that a laser diameter measuring system is compatible to control the diameter tolerances of the filaments.

Further, an exemplary embodiment of the present invention provides a prosthetic system comprising a magnetic system configured to yield a specific pre-determined stray magnetic field, but which requires a software-controlled magnetization process to adjust the orientation and/or polarity of the magnetic system (before or during manufacture). The software-controlled magnetization process enables precision control over the magnetic field of the final product. The magnetization system may comprise an electromagnet, for example, a water-cooled electromagnet powered by a low-voltage power supply such as a Siemens® NTN 35000-200 or equivalent. The magnetization system allows new magnetic designs to be created on a computer alongside prosthetic engineers and reproduced rapidly, with a precision of well under one millimeter. It is envisioned that the magnetization system may involve locally magnetizing, or aligning, the magnetic particles if applicable during the solidification process of the surrounding substrate.

In this way, the magnetic system may provide improved attraction forces, repulsion forces, and/or alignment for the prosthetic system, which is impossible with conventional standard magnet plugs or plates. For example, the magnetic system may be engineered to hold certain components of the prosthetic in proper alignment when properly attached/ engaged. The magnetic system also may be engineered with a distinct and separate force curve to also lightly repel aligned or partially aligned if the components are too close. In the end, the magnetic system may operate at least in part as a polymagnetic spring and/or polymagnetic latch and/or equivalent.

In order to accomplish these ends, the magnetization system may apply, at least in part, Barker correlation codes from communications theory. More specifically, when mathematical waves or curves such as sine waves are in phase, they are additive and reinforcing. When they are out of phase, they can actually cancel each other out, entirely or in part. Barker correlation codes are unique sequences of + and − in a function such that when certain parameters line up, the two functions resonates with one another, but when certain parameters do not line up, or are shifted, the resonance between the two functions falls off. Instead of curves being in and out of phase by time (communications theory), the patterns of magnetic north and south poles can be in and out of phase by position—physically shifting or offsetting the poles past each other. The magnetization system may calculate based on the Barker code behavior to pattern magnetic north and south poles in the magnetic system. This results in an overall system and method where the final product is specifically tailored to (1) how tightly the magnetic system/components attract and hold one another, (2) how abruptly the attraction/repulsion falls off as the magnetic system/components are shifted/displaced/pivoted with respect to one another, and/or (3) how limited or not limited the field strength extends to avoid interference with external objects.

Further, an exemplary embodiment of the present invention an exemplary embodiment of the present invention provides an exemplary embodiment of a prosthetic joint comprising correlated magnet pairs programmed to attract and/or repel with a prescribed force and engagement distance, or to attract and/or repel at a certain spatial orientation. The correlated magnet pairs incorporate correlated patterns of magnets or magnetic particles/granules with alternating polarity, designed to achieve a desired force curve profile. The correlated magnets may be engineered to interact only with other magnetic structures that have been similarly engineered to respond, for example, with others that yield a cog-shaped field. The correlated magnet pairs may be programmed to attract or repel with a prescribed force and engagement distance, or, to attract or repel at certain spatial orientations. The correlated magnet pairs also may be programmed to attract and repel at the same time by varying the multipole structure of the maxels by varying size, location, orientation, and saturation. The maxels may range from 1 mm to 4 mm in one exemplary embodiment.

The Figures and the related description are offered for illustrative purposes and depict exemplary embodiments of a magnetic joint prosthetic in accordance to the solution. As such, the exemplary embodiments shown in the Figures do not illustrate all features and aspects that may be included in a given embodiment of the artificial magnetic joint prosthetic in accordance to the solution. For instance, it is envisioned that the magnetic joint prosthetic according to the solution may be manufactured into any given joint suitable for the implantation into a human living body and/or may be constructed from any combination of materials depending on the intended use of the particular embodiment. The encapsulated magnetic particles/granules of an embodiment may be dispersed into a solution of methyl methacrylate (PMMA), polyethylene(PE) or a biocompatible oxide ceramic, etc. 3D Metal Printing of Nano-Magnetic Prosthesis It is envisioned that a technology software platform will be used for the design of a patient-specific prosthetic implant. An algorithm based on the patients anthropometrics converts the two dimensional CT scan of the joint to a three dimensional (3D) model by mapping the articular surface of the joint and defining the area of disease and healthy joint. It is envisioned that the software will use this information to design the implants that will match precisely to the 3D model of the joint. In this 3D environment, it is envisioned that the software will recreate the natural J curve of the joint correcting for any underlying arthritic deformity such as bone spurs or flattening of the joint. The software will then build either the tibial and femoral implants for the knee or the acetabular component, femoral head and femoral stem for the hip to match the unique size and shape of the joint eliminating pain or discomfort.

Further, it is envisioned that a 3D metal printer may be used to create the nanomagnetic prosthetic by way of additive manufacturing method. Additive manufacturing allows for the fabrication of complex parts that cannot be manufactured by traditional machines, creating a patient-specific prosthetic joint that is efficient and high performing. This method is the process of creating 3D objects in which layers of materials, in this case powder nanomagnetic particles and other embodiments thereof, are formed to create the prosthetic joint.

As is understood by one of ordinary skill in the art, there are major processes for metal 3D printing. It is envisioned but not limited to one of ordinary skill in the art to use either the powder bed fusion process, binder jet process, freeform direct laser deposition process and other known processes thereof. Further, it is envisioned that the 3D CT scan may be converted to a virtual image for the purpose of verifying that the design is anatomically functional. This validated 3D design may then be printed in plastic creating an actual 3D part versus a virtual design by a common process known to one in ordinary skill of art. It is further envisioned that proposed fabrication of the nanomagnetic prosthesis by way of using a 3D metal printer, may use nanomagnetic powder and other embodiments thereof. The nanomagnetic powder and other embodiments thereof, may be spread onto the substrate plate and a powder reservoir of the 3D metal printer.

An exemplary printer has a high-powered watts laser and a blade most commonly used, will carry the powder across the substrate plate building layers having thickness ranges of 20.0 to 100.0 µm, or 1.0 to 100.0 µm. Once the powder layer is distributed, the laser may either selectively melt or bound the nanomagnetic particles together to form a solid part building layer by layer until the shape of a knee or hip joint, but not limited to these particular joints to one of ordinary skill in the art, is formed. Once the nanomagnetic joint is printed, it is envisioned that the joint may be scanned again to measure the dimensions and validate that the criteria for the design.

Anthropometrics

It is envisioned that weight may be measured to the nearest 0.1 kg (with the subject's shoes, socks, and bulky clothing removed), with a single pair of electronic scales that will calibrate the weight. Height may be measured to the nearest 0.1 cm (with shoes and socks removed) using a stadiometer. Body mass index (BMI) may be calculated as weigh (kg)/height (m$^2$).

Computerized Tomography (CT Scan)

A computerized tomography (CT) scan combines a series of X-ray images taken from different angles and uses computer processing to create cross-sectional images of the bones to provide more detailed information about the structure of the bones. It is envisioned that a CT scan may be used to visualize the whole joint of both the healthy knee or hip joint and the diseased knee or hip joint to allow for a customized fit, for example.

Certain embodiments disclosed will become more apparent from the drawings and following description.

Figure 1A:

FIG. 1 is an illustration of an exemplary embodiment of a prior art basic artificial knee joint structure showing a diseased knee replaced by an artificial joint made of either metal alloys, high grade plastics or polymers, in which a plastic spacer in placed between the femoral and tibial component. As can be seen, FIG. 1 illustrates a knee joint damaged by trauma or disease 100A. During a knee arthroplasty procedure, portions of the damaged cartilage and bone is removed from the surface of the knee joint and replaced with man-made surface of metal and/or plastic 100B. In the FIG. 1 illustration a femoral component composed of either metal alloys, high grade plastics or polymers 100C, a plastic spacer 100D, and tibia component composed of either metal alloys, high grade plastics or polymers 100 E can be seen.

In an exemplary embodiment of a healthy, well aligned knee joint, the mechanical axis which is the line extending from the center of the hip joint to the middle of the ankle joint passes through the middle of the knee. Only when the mechanical axis passes through the center of the knee joint, the stresses on the knee joint surfaces are uniform in all areas of the joint and well balances. In many knee joint diseases, the mechanical axis is disturbed and does not pass through the center of the joint. This disturbance results in the overload of distinct areas of the knee joint leading to their damage. The surgeon must restore the mechanical axis of the knee joint during the total replacement surgery. If a total knee prosthesis is not realigned properly the joint will become overloaded leading to dislocation, loosen or break down.

Figure 2B:
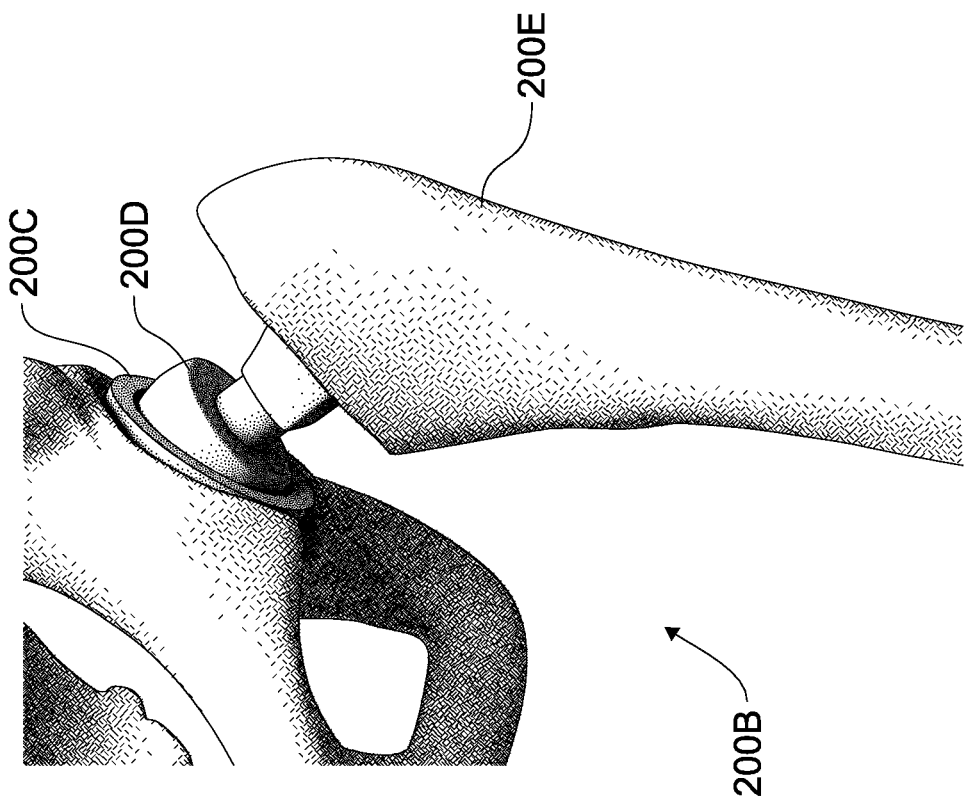
FIGS. 2A and 2B collectively illustrate an exemplary embodiment of a prior art basic artificial hip joint structure showing a diseased hip replaced by an artificial joint made of either metal alloys, high grade plastics or polymers, in which a plastic spacer in placed between the acetabular component and femoral head.
Figure 2A:
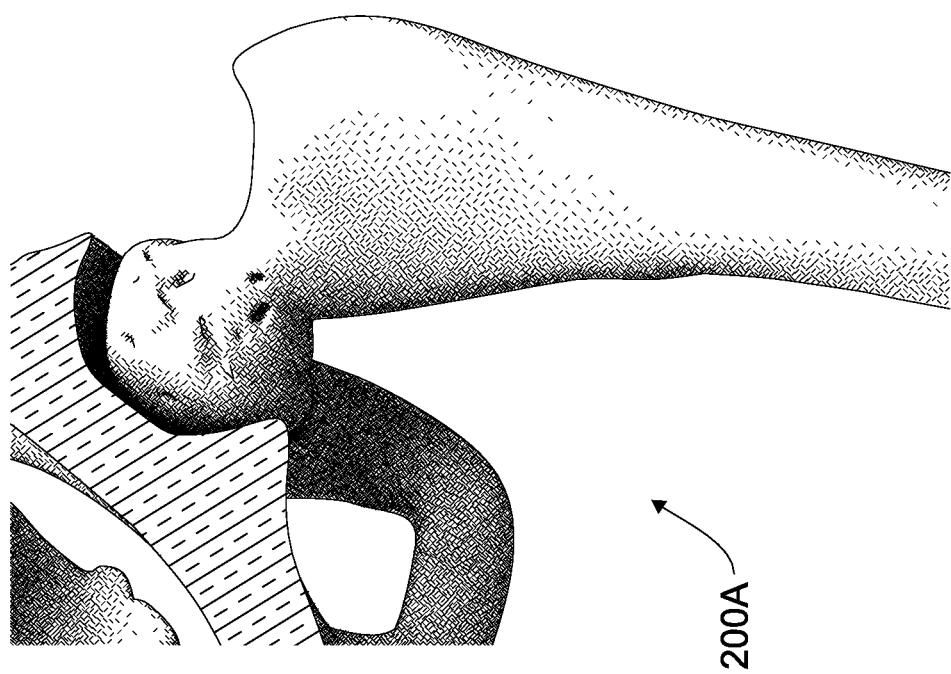

FIG. 2 is an illustration of an exemplary embodiment of a prior art basic artificial hip joint structure showing a diseased hip replaced by an artificial joint made of either metal alloys, high grade plastics or polymers, in which a plastic spacer in placed between the acetabular component and femoral head. As can be seen, FIG. 2 illustrates, a hip joint damaged by trauma or disease 200A. During a hip arthroplasty procedure, portions of the damaged cartilage and bone is removed from the surface of the knee joint and replaced with man-made surface of metal and/or plastic 200B. In the FIG. 2 illustration, an acetabular component 200C, a femoral head 200D, a femoral stem 200E all composed of either metal alloys, high-grade plastics or polymers can be seen.

Figure 3:
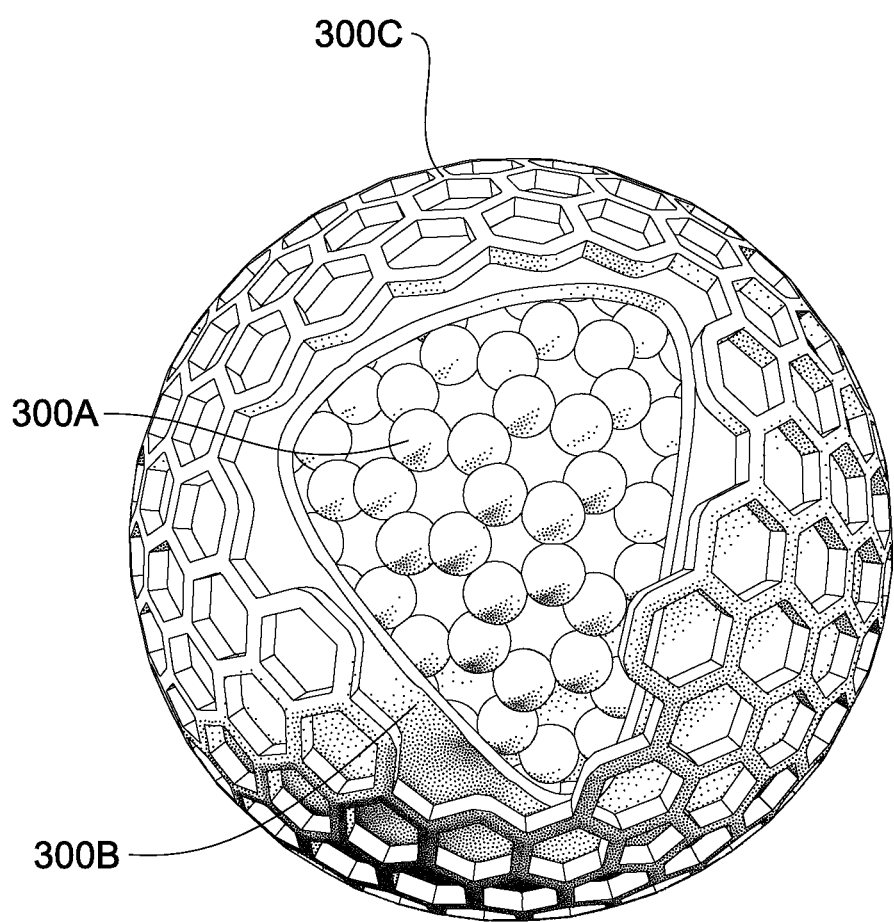
FIG. 3 is an illustration of an exemplary embodiment of a magnetic nano-particle with a magnetic core and a biocompatible coating.
Figure 4A:
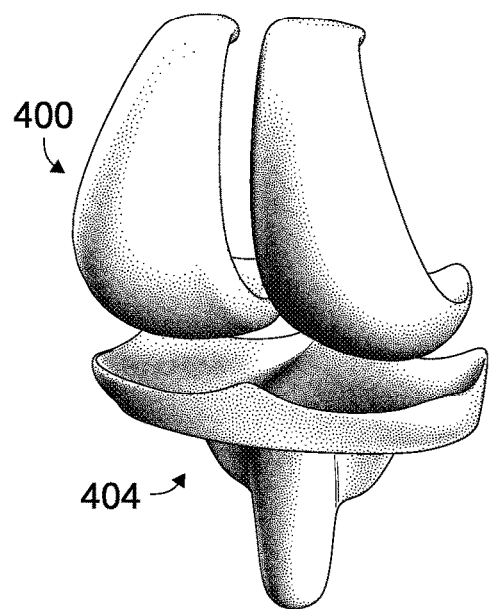
FIGS. 4A, 4B, 4C and 4D illustrate perspective views of exemplary embodiments of a detached nano-magnetic knee replacement in accordance with the solution, including components composed of hardened magnetic nano-particles that either partially coat or fully coat the joint.
Figure 4B:
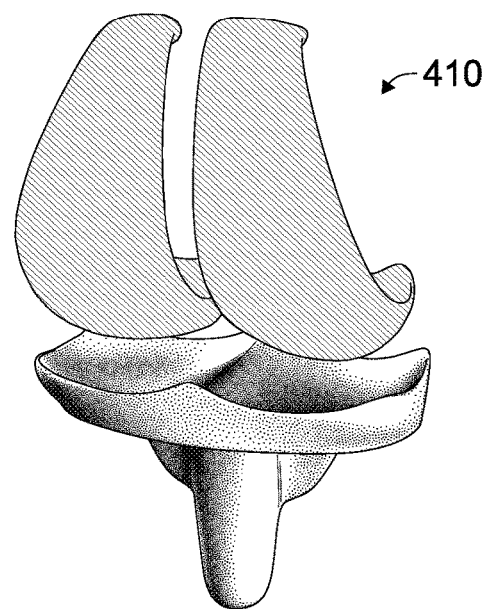
Figure 4C:
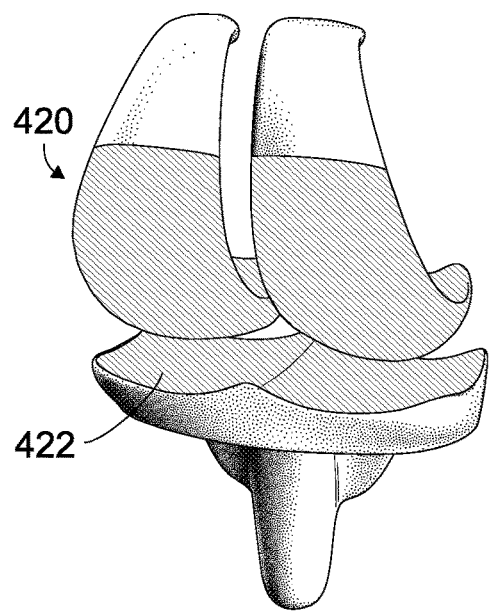
Figure 4D:
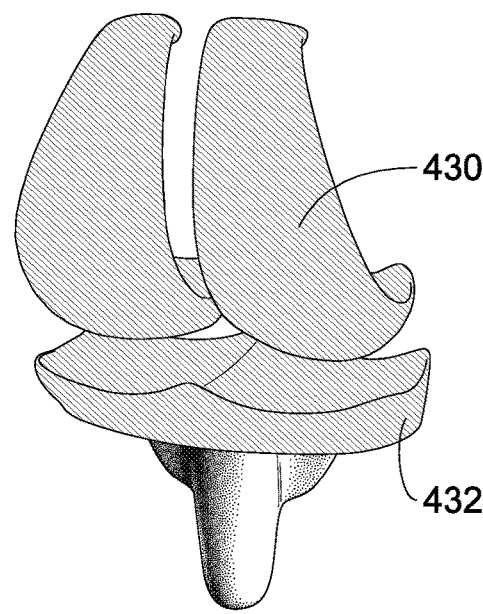
Figure 5A:
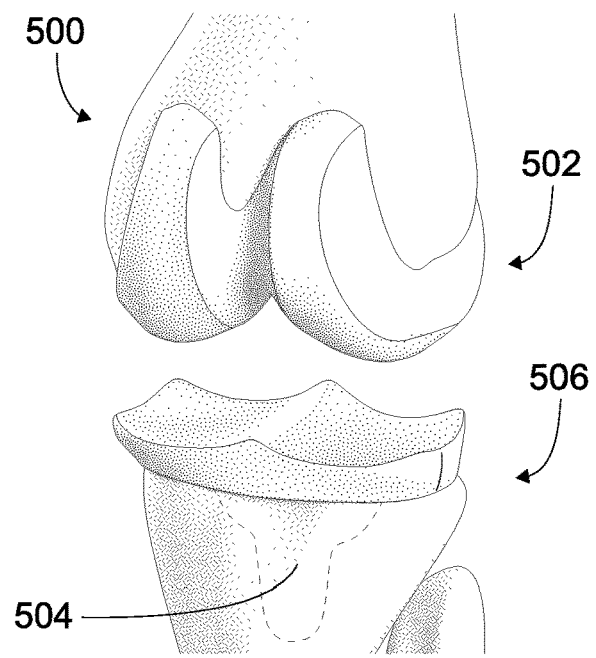
FIGS. 5A, 5B, 5C and 5D illustrate perspective views of exemplary embodiments of an attached nano-magnetic prosthesis to its respective knee joint in accordance with the solution, including components composed of hardened magnetic nano-particles that either partially coat or fully coat the joint.
Figure 5B:
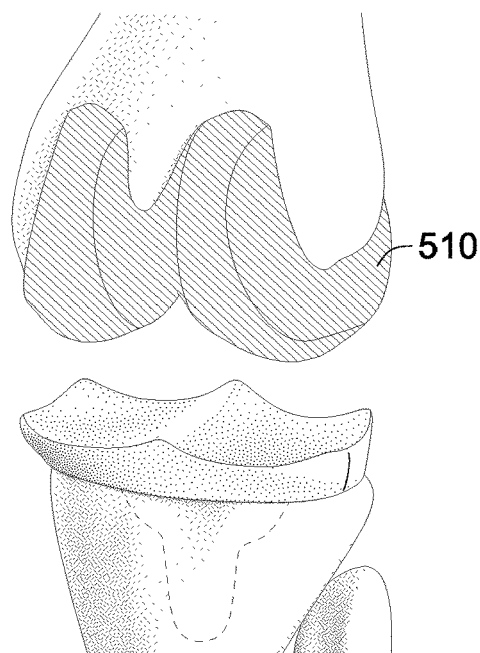
Figure 5C:
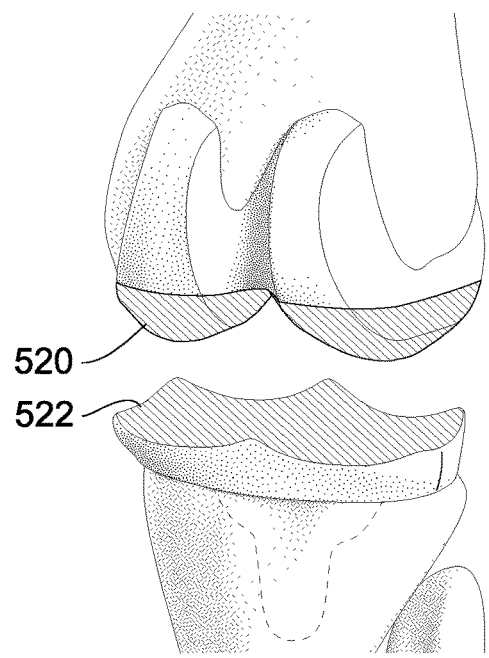
Figure 5D:
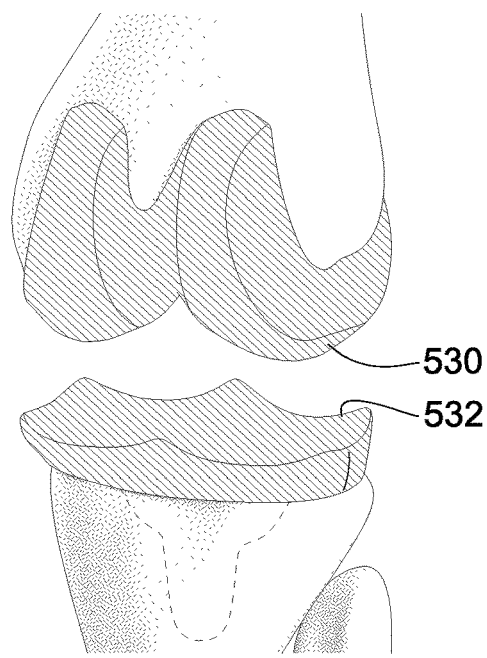
Figure 6A:
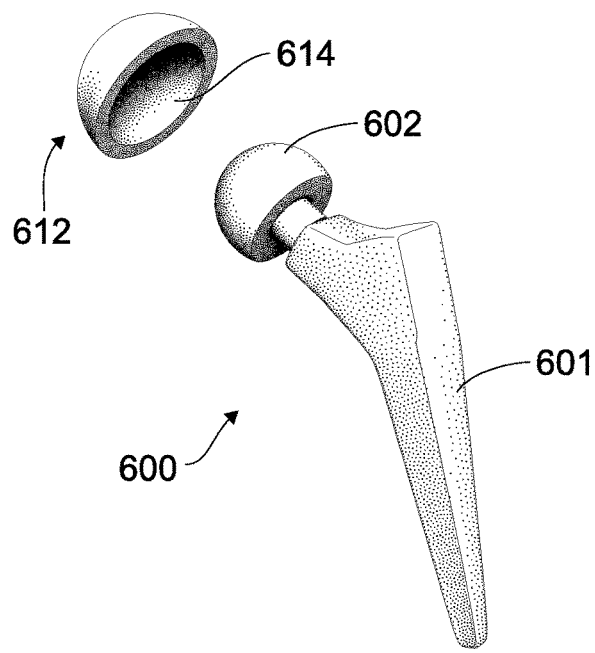
FIGS. 6A, 6B, 6C and 6D illustrate perspective views of exemplary embodiments of a detached nano-magnetic hip replacement in accordance with the solution, including components composed of hardened magnetic nano-particles that either partially coat or fully coat the joint.
Figure 6B:
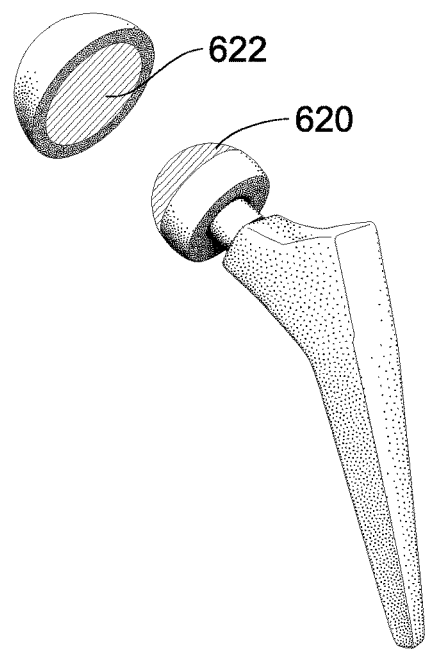
Figure 6C:
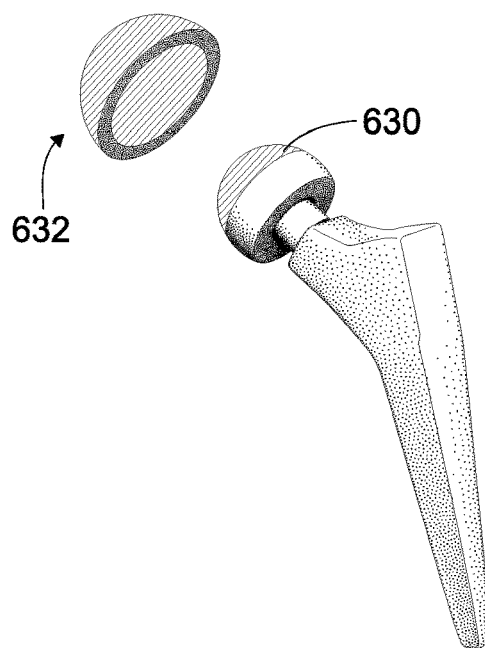
Figure 6D:
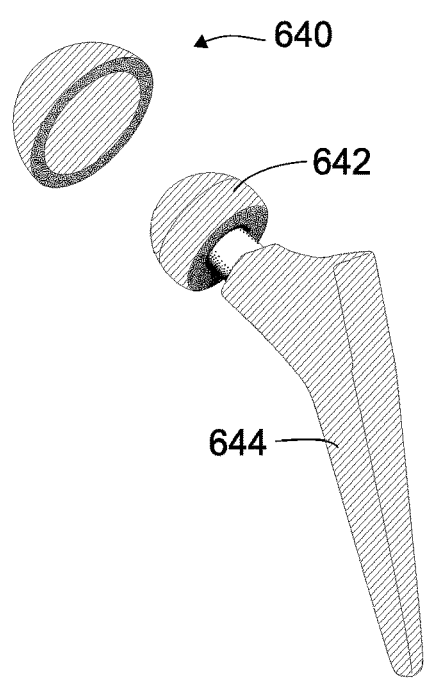
Figure 7A:
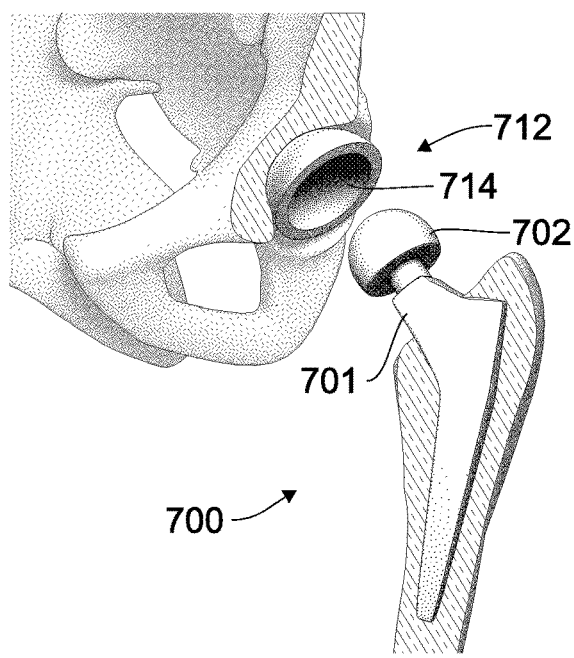
FIGS. 7A, 7B, 7C and 7D illustrate perspective views of exemplary embodiments of an attached nano-magnetic prosthesis to its respective hip joint in accordance with the solution, including components composed of hardened magnetic nano-particles that either partially coat or fully coat the joint.
Figure 7B:
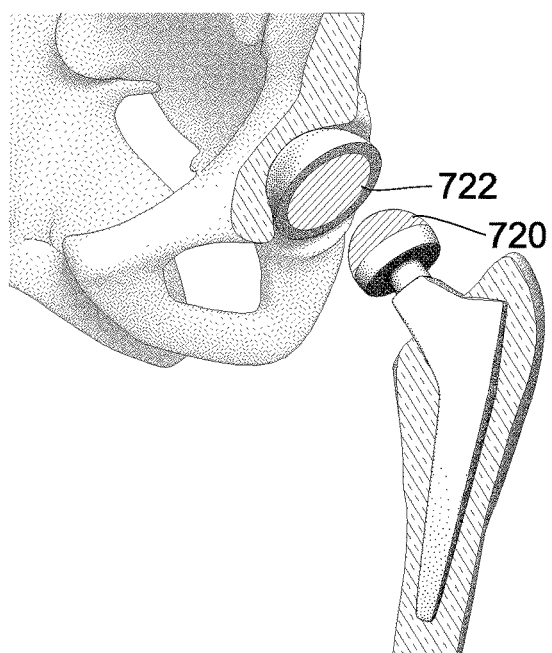
Figure 7C:
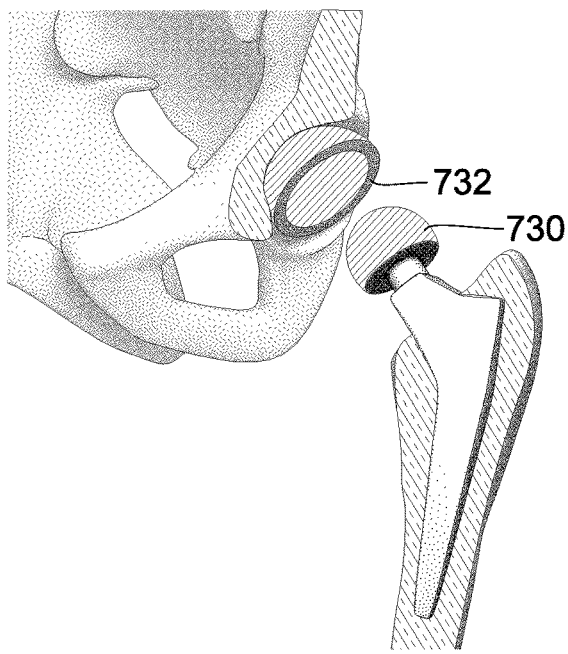
Figure 7D:
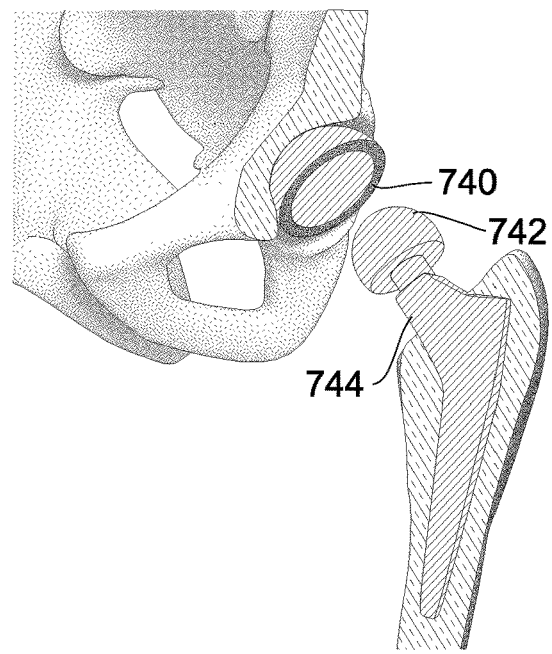

FIG. 3 is an illustration of an exemplary embodiment of a magnetic nano-particle with a magnetic core and a biocompatible coating. This functional magnetic nanoparticle consists of a number of components; the magnetic core 300A, the protective coating 300B and the biocompatible surface coating 300C. Advantageously, it is envisioned that the magnetic core materials 300A will be composed of the preferred embodiment according to the solution of either iron oxide, iron alloyed, or rare earth metal alloyed-based materials thereof. It is envisioned that the magnetic core nanomaterial will have a protective coating 300B with a preferred embodiment according to the solution of either natural polymers such as carbohydrates and proteins thereof; synthetic organic polymers such as poly(ethyleneglycol) (PEG), polyvinvyl alcohol (PVA) and poly-L-lactic acid (PLA) thereof; silica and gold. Furthermore, to control the biological response in the material, it is envisioned that the biocompatible surface coating 300C will have the preferred embodiment according to the solution of a bio-compatible protein, such as tropoelastin, collagen, albumin, keratin, fibronectin, actin, mysosin, fibrinogen, thrombin, aprotinin, antithrombin thereof and a bio-compatible antimicrobial such as a parylene polymer thereof.

Optionally, the biocompatible surface may be a biocompatible film deposited on the surface of the nano-magnetic particle. Optionally, the nano-magnetic particle may have the biocompatible surface coating applied by dipping the particle into a solution containing bio-compatible proteins and antimicrobials. Optionally, the nano-magnetic particle may have the biocompatible surface coating applied by spraying the biocompatible protein and antimicrobial solution to allow for a controlled application and uniform coating. The present solution is not limited to a particular material onto which a magnetic nanoparticle is formed, the underlying material used for the nano-magnetic prosthesis may be chosen according to a variety of factors, such a mechanical stability and ease of function.

FIG. 4 is a perspective view of an exemplary embodiment of a detached nano-magnetic knee replacement in accordance with an exemplary embodiment to the solution, including components composed of hardened magnetic nano-particles that either partially coat or fully coat the joint. One embodiment for knee joint replacements as shown in FIG. 4A, which includes femoral head component 400 and a tibia head component 404. Both femoral head 400 and tibial component 404 components have hardened magnetic nano-particles placed in each component. In the depicted embodiment of FIG. 4B, hardened magnetic nano-particles are fully embedded on the upper top portion of the femoral head 410. In the depicted embodiment of FIG. 4C, hardened magnetic nano-particles are partially embedded on the lower top portion of the femoral head 420 and the upper top portion of the tibia component 422. In the depicted embodiment of FIG. 4D, hardened magnetic nano-particles are fully embedded in the femoral head 430 and the tibia component 432.

FIG. 5 is a perspective view of an exemplary embodiment of an attached nano-magnetic prosthesis to its respective knee joint in accordance with an exemplary embodiment to the solution, including components composed of hardened magnetic nano-particles that either partially coat or fully coat the joint. One embodiment for knee joint replacements is shown in FIG. 5A, which comprises femoral component 500 comprising a femoral head component 502 and a tibia component 504 comprising a tibia head component 506. Both femoral head 500 and tibial component 504 components have hardened magnetic nano-particles placed in each component to give a more stable connection when align at a boundary of the predefined functional range of motion. In the depicted embodiment of FIG. 5B, hardened magnetic nano-particles are fully embedded on the upper top portion of the femoral head 510. In the depicted embodiment of FIG. 5C, hardened magnetic nano-particles are partially embedded on the lower top portion of the femoral head 520 and the upper top portion of the tibia component 522. In the depicted embodiment of FIG. 5D, hardened magnetic nano-particles are fully embedded in the femoral head 530 and the tibia component 532.

The embedment of the nano-magnetic particles in the anterior and posterior surface areas of the knee joint components are determined in relation to the anticipated physiological placement of the components when in contact with the condyles in femoral and tibia, for example, and may be uniquely defined by positional unique anatomical features of the components (e.g., where the components comprise anatomical features designed to be secured in a single unique anatomical orientation such as, e.g., the J-shaped curve extending from posterior side of femoral to the anterior articular surface of the tibia), or by actual designation markings provided on the component specifying which areas should be positioned anteriorly or posteriorly when secured. More particularly, e.g., where a femoral head attached to an essential tibia component is employed, one section of the surface head of the femur may be marked as the designated posterior and the tibia surface may be marked as anterior (i.e. the femoral head and tibia having fully embedded nano-magnetic particles therein as oppose to partial), and the surgeon may then accordingly correctly position such component based on such marking. The markings may be in the form well known to those skilled in the art. The components may further be designated as medial and lateral condyle, allowing for the further specific whole or partial embedment of nano-magnetic particles aligned laterally or medially in accordance with further specific embodiments.

FIG. 6 a perspective view of an exemplary embodiment of a detached nano-magnetic hip replacement in accordance with an exemplary embodiment to the solution, including components composed of hardened magnetic nano-particles that either partially coat or fully coat the joint. One embodiment for hip joint replacements is shown in FIG. 0.6A, which comprises femoral component 600 comprising a shaft portion 601 and a femoral head portion 602 having a commonly spherical shaped socket portion. Acetabular component comprises a cup shaped socket portion 612 fixed to the pelvis. Socket portion 614 has an inner concave surface generally corresponding to the spherical surface of the femoral head portion. The femoral head 600 and acetabular socket 602, 612 components have hardened magnetic nano-particles placed in each component. In the depicted embodiment of FIG. 6B, hardened magnetic nano-particles are partially embedded on the upper top portion of the femoral head 620 and the lower socket portion of the inner concave surface of the acetabular component 622. In the depicted embodiment of FIG. 6C, hardened magnetic nano-particles are partial embedded in the top upper portion of femoral head 630 and the entire socket portion and inner concave surface of the acetabular component 632. In the depicted embodiment of FIG. 6D, the entire acetabular component 640, femoral head 642 and femoral stem 644 are composed of hardened magnetic nano-particles.

FIG. 7 is a perspective view of an exemplary embodiment of an attached nano-magnetic prosthesis to its respective hip joint in accordance with an exemplary embodiment to the solution, including components composed of hardened magnetic nano-particles that either partially coat or fully coat the joint. One embodiment for knee joint replacements as shown in FIG. 7A, femoral component 700 comprises a shaft portion 701 and a femoral head portion 702 having a generally spherical shaped socket portion. Acetabular component comprises a cup shaped socket portion 712 fixed to the pelvis. Socket portion 714 has an inner concave surface generally corresponding to the spherical surface of the femoral head portion, whereby the spherical surface of the femoral head portion is relatively displaceable with respect to the concave surface of the acetabular component over to predefines functional range of motion of the femoral head portion when positioned within the acetabular component. The femoral head 700 and acetabular socket 702, 712 components have hardened magnetic nano-particles placed in each component to give a more stable connection when align at a boundary of the predefined functional range of motion. In the depicted embodiment of FIG. 7B, hardened magnetic nano-particles are partially embedded on the upper top portion of the femoral head 720 and the lower socket portion of the inner concave surface of the acetabular component 722. In the depicted embodiment of FIG. 7C, hardened magnetic nano-particles are partial embedded in the top upper portion of femoral head 730 and the entire socket portion and inner concave surface of the acetabular component 732. In the depicted embodiment of FIG. 7D, the entire acetabular component 740, femoral head 742 and femoral stem 744 are composed of hardened magnetic nano-particles.

The embedment of the nano-magnetic particles in the anterior and posterior surface areas of the hip joint components are determined in relation to the anticipated physiological placement of the components when secured to the femur and pelvis, and may be uniquely defined by positional unique anatomical features of the components (e.g., where the components comprise anatomical features designed to be secured in a single unique anatomical orientation such as, e.g., the curve of the femoral stem portion having an attached femoral head to uniquely fit the left or right femur), or by actual designation markings provided on the component specifying which areas should be positioned anteriorly or posteriorly when secured. More particularly, e.g., where an femoral head attached to an essential circumferential symmetric acetabular cup component is employed, one section of the surface head of the femur may be marked as the designated anterior and the cup surface may be marked as posterior (i.e. the femoral head and acetabular cup having fully embedded nano-magnetic particles therein as oppose to partial), and the surgeon may then accordingly correctly position such component based on such making. The markings may be in the form well known to those skilled in the art. The components may further be designated as lateral or medial sides, allowing for the further specific whole or partial embedment of nano-magnetic particles aligned laterally or medially in accordance with further specific embodiments.

Figure 8:
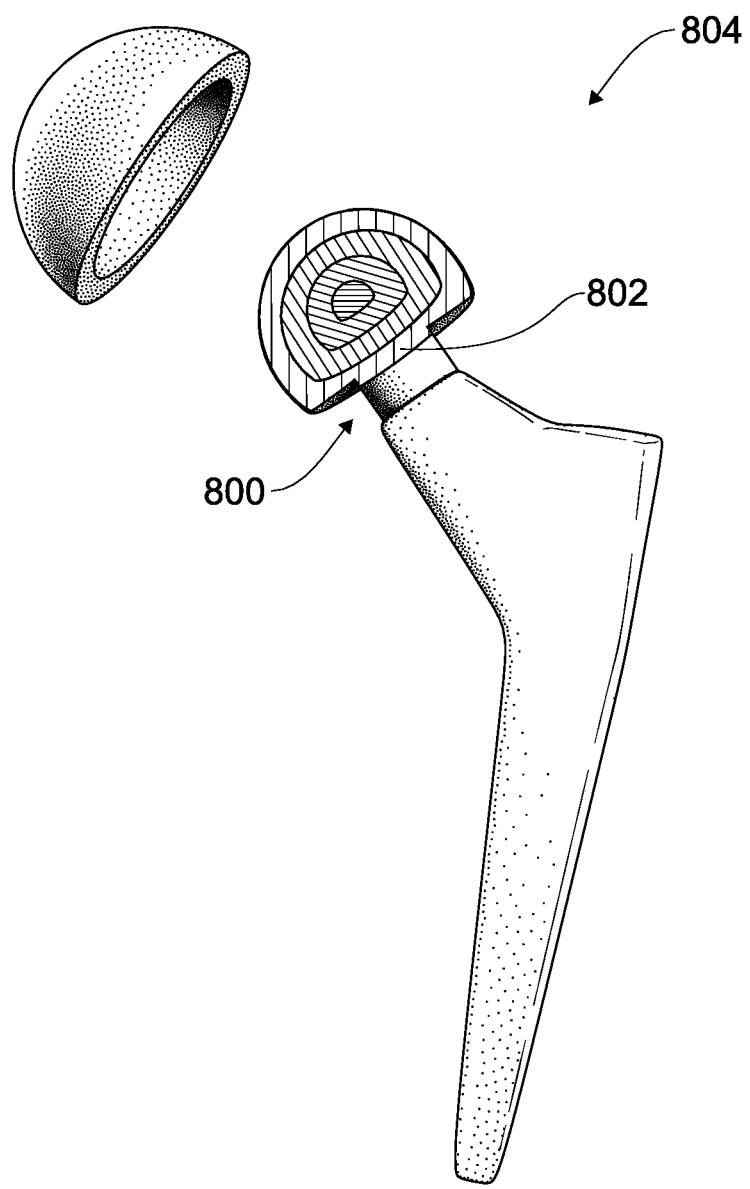
FIG. 8 is a side perspective view of an exemplary embodiment of a prosthetic system comprising a magnetic system configured to yield a specific pre-determined stray magnetic field of complex form.

FIG. 8 is a side perspective view of an exemplary embodiment of a prosthetic system comprising a magnetic system configured to yield a specific pre-determined stray magnetic field of complex form. Further, the magnetic system 800 was engineered via computer software, before and during manufacture, which adjusts the shape until all requirements for the desired magnetic profile are met. In this particular embodiment, the magnetic system 800 comprises magnetic patterns, shapes, and/or bulk geometric structures embedded within the prosthetic material. Once the desired geometric shape and magnetic profile was computed, the additive manufacturing system used filament(s) of a magnetic particle held together by a polymer binding material. The additive manufacturing system prepared the additive material(s) for application and applied them for variable magnetic compound fraction distribution 802, wherein the saturation magnetization was adjusted during the printing process, or prepared for adjustment, to obtain the desired external field 804.

In particular, a twin-screw mixing extruder was used to mix magnetic filaments/source material with bio-prosthetic preferred substrate material/filaments. The magnetic source material and the substrate material also were compounded, extruded, and characterized or prepared to be characterized for the printing process. The result is a magnetic system 800 in the prosthetic comprising a component or portion or region or gradient 802 composed of roughly between 70-90% magnetic material and 30-10% substrate in some regions, and also roughly between 40-65 vol. % magnetic material in other regions.

Further, as stated above, the prosthetic system may comprise a magnetic system configured to yield a specific pre-determined stray magnetic field 804, but which requires a software-controlled magnetization process to adjust the orientation and/or polarity of the variable magnetic compound fraction distribution 802 (before or during manufacture). The software-controlled magnetization process enables precision control over the magnetic field 804 of the final product and the areas of high and low gauss.

In this way, the magnetic system 800 may provide improved attraction forces, repulsion forces, and/or alignment for the prosthetic, which are impossible with conventional standard magnet plugs or plates. For example, the magnetic system may be engineered to hold certain components of the prosthetic in proper alignment when properly attached/engaged. The magnetic system also may be engineered with a distinct and separate force curve to also lightly repel aligned or partially aligned if the components are too close. In the end, the magnetic system may operate at least in part as a polymagnetic spring and/or polymagnetic latch and/or equivalent.

Figure 9A:
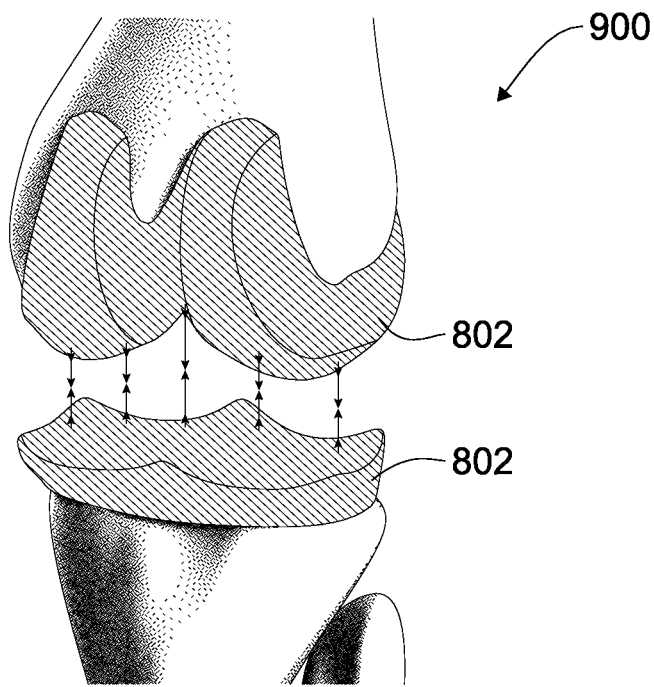
FIGS. 9A and 9B are perspective views of an exemplary embodiment of a prosthetic system like that of FIG. 8, but to illustrate the repulsive and attraction force possibly involved in the prosthetic system.
Figure 9B:
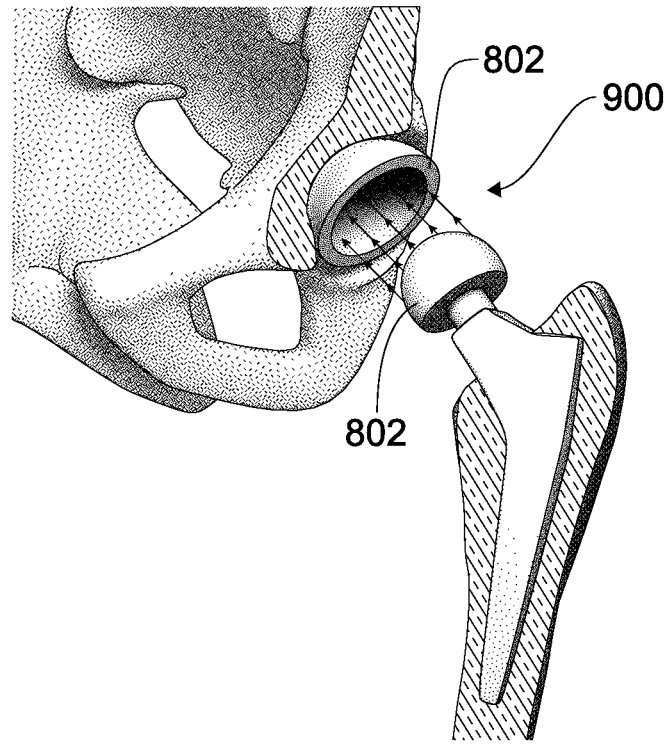
Figure 10:
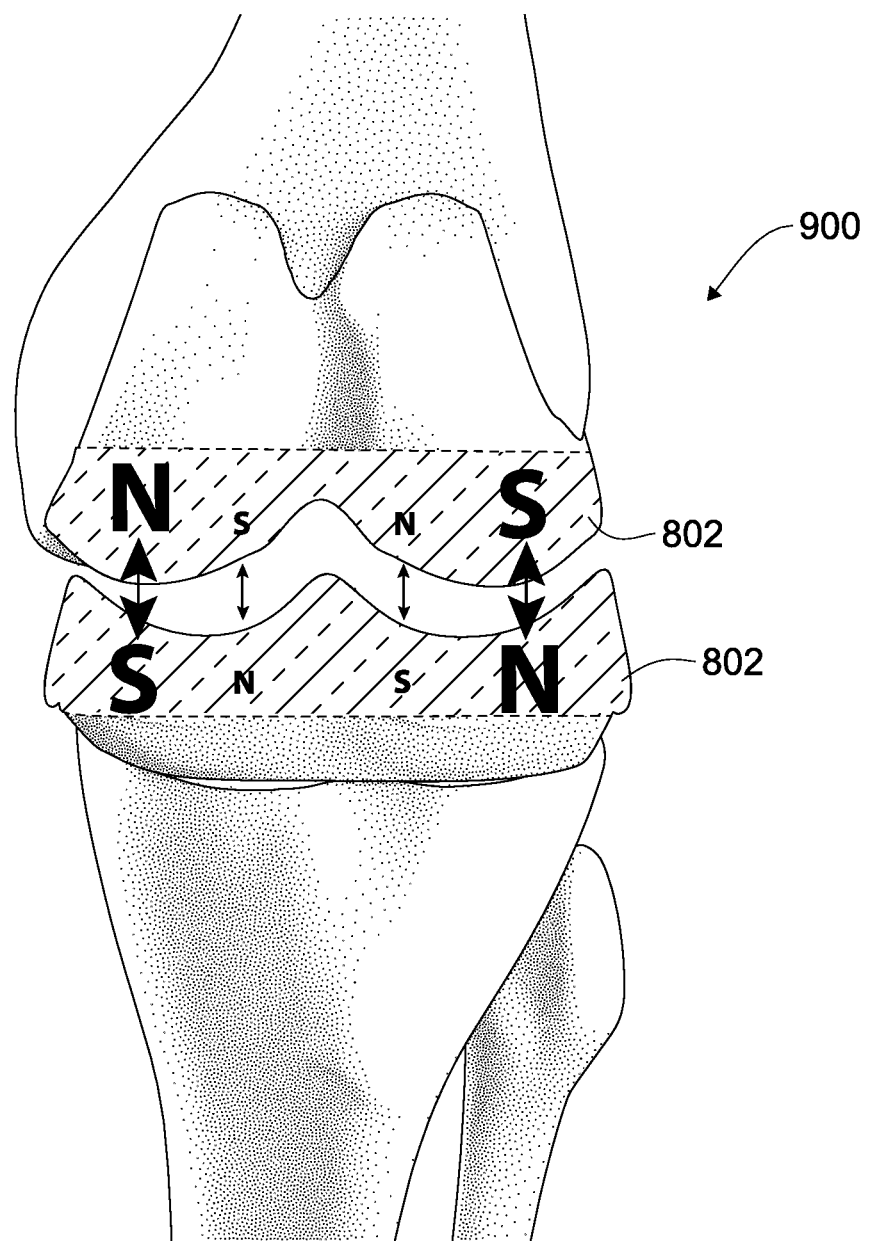
FIG. 10 is a magnified perspective views of an exemplary embodiment of a prosthetic system like that of FIG. 9A, but to illustrate the smooth transition between strong and weak magnetism.

FIG. 9 are perspective views of an exemplary embodiment of a prosthetic system like that of FIG. 8, but to illustrate the repulsive and attraction force possibly involved in the prosthetic system. FIG. 9A in particular is a front perspective view of an exemplary embodiment of the prosthetic system 900. FIG. 9B in particular is a side cross-section view of an exemplary embodiment of the prosthetic system 900. Similarly, FIG. 10 is a magnified perspective view of an exemplary embodiment of a prosthetic system like that of FIG. 9A, but to illustrate the smooth transition between strong and weak magnetism. FIG. 10 in particular is a front perspective view of an exemplary embodiment of the prosthetic system 900 and a portion of its variable magnetic compound fraction distribution 802.

Figure 11:
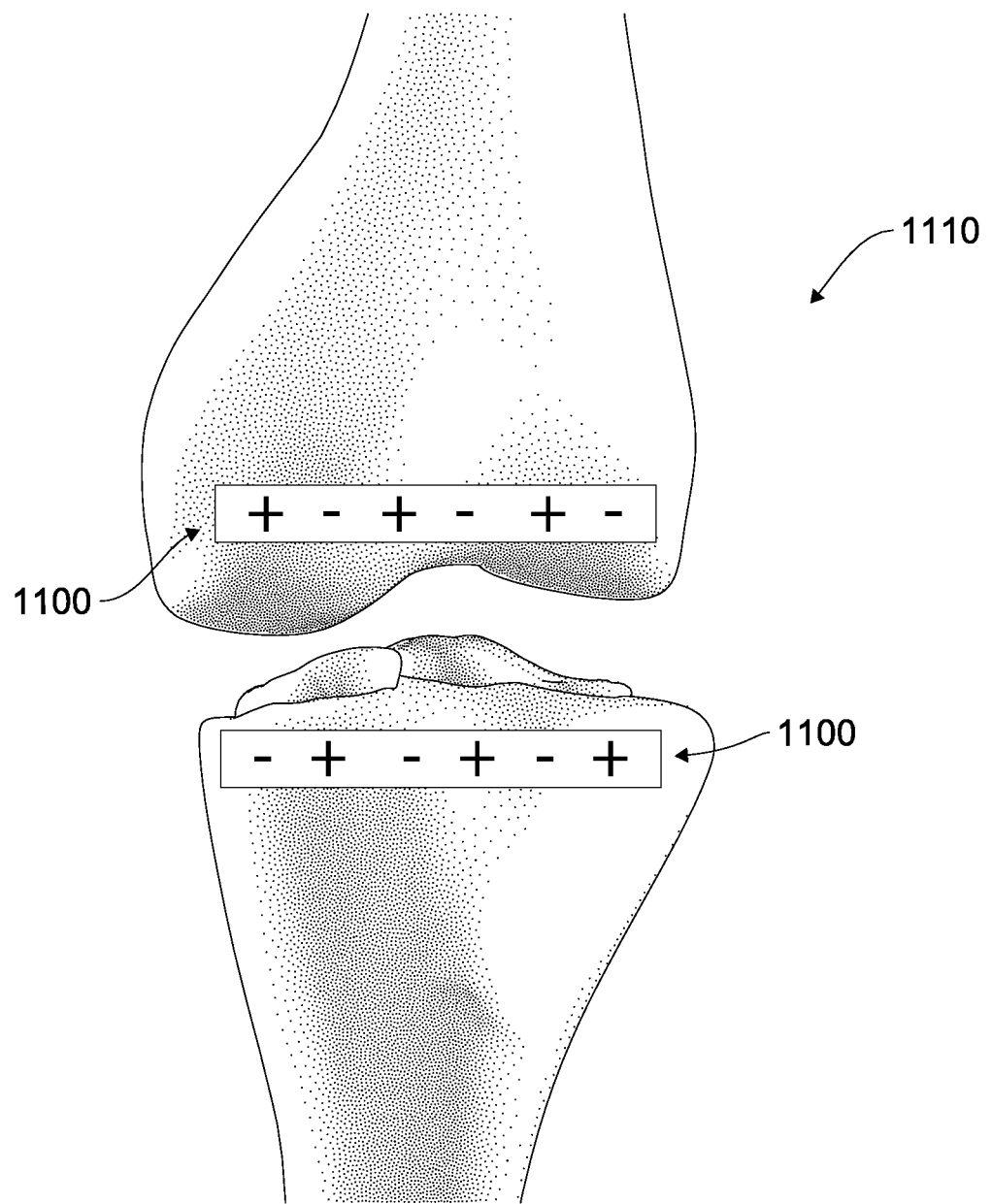
FIG. 11 is a front perspective view of an exemplary embodiment of a minimized prosthetic system comprising a correlated magnet pair 1100 programmed to attract and/or repel with a prescribed force and engagement distance, or to attract and/or repel at a certain spatial orientation.

FIG. 11 is a front perspective view of an exemplary embodiment of a minimized prosthetic system comprising a correlated magnet pair 1100 programmed to attract and/or repel with a prescribed force and engagement distance, or to attract and/or repel at a certain spatial orientation. The correlated magnet pair 1100 incorporates correlated patterns of magnets or magnetic particles/granules with alternating polarity, designed to achieve a desired force curve profile. The correlated magnets 1100 are engineered to interact only with other magnetic structures that have been similarly engineered to yield a cog-shaped field. The correlated magnet pair 1100 are programmed to attract or repel with a prescribed force and engagement distance, and, to attract or repel at certain spatial orientations. The correlated magnet pair 1100 also is programmed to attract and repel at the same time by varying the multipole structure of the maxels by varying size, location, orientation, and saturation.

In particular, the correlated magnet pair 1100 apply, at least in part, Barker correlation codes. The correlated magnet pair 1100 may be based on the Barker code behavior to pattern magnetic north and south poles in the magnetic system for a particular desired stray field. In this particular embodiment, however, as compared to the embodiment of FIGS. 8-10, for example, the correlated magnet pair 1100 are embedded within the bone of the articulation joint 1110 to be repaired.

Referring now to FIG. 12, the FIGS. are a flow chart of an exemplary embodiment of a method of manufacturing the magnetic prosthetic of FIGS. 9-10, for example. One of ordinary skill in the art understands that the exemplary method 1200 may be performed by various manufacturing means that do not limit the scope of the present disclosure.

Figure 12A:
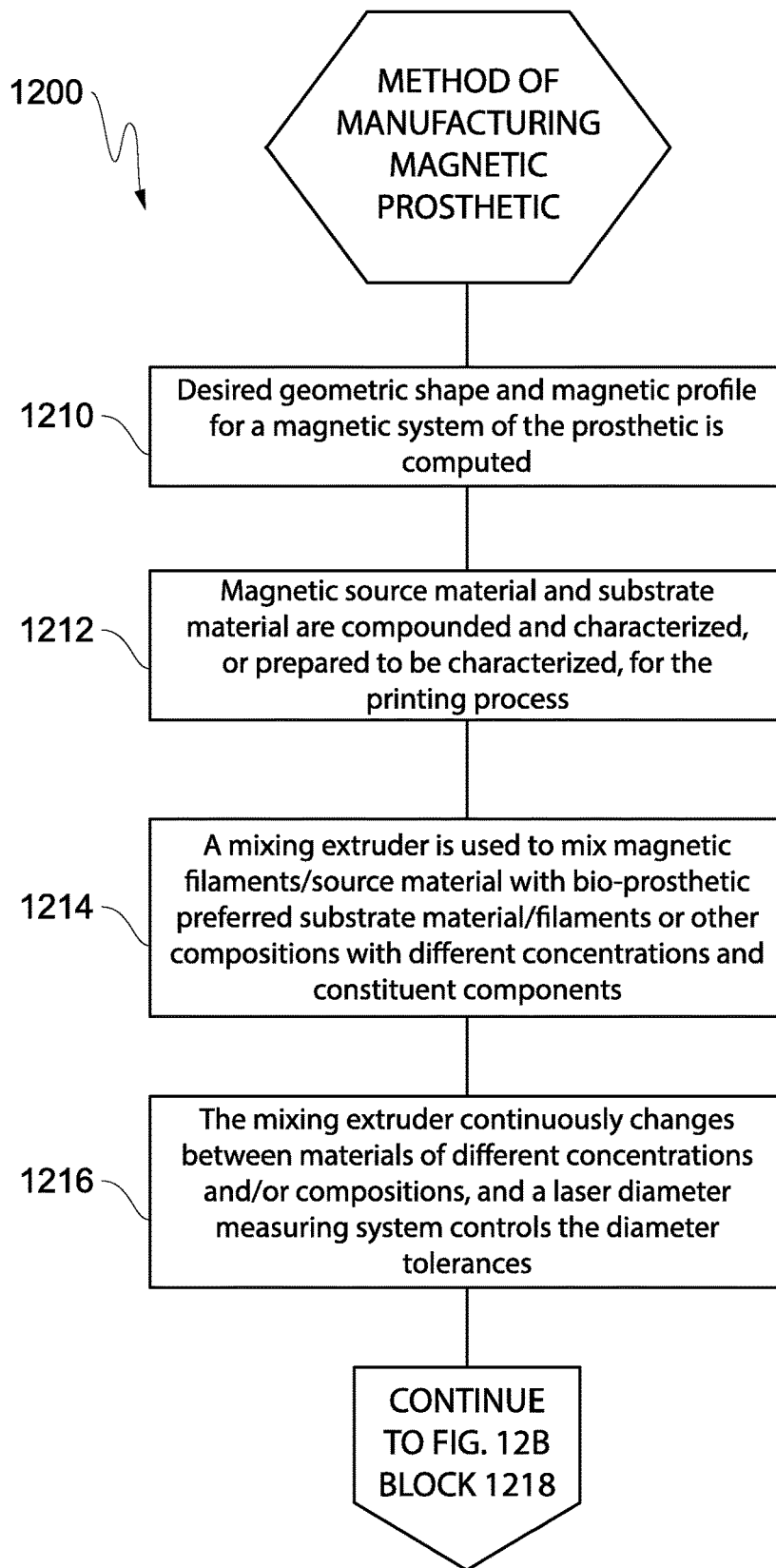
FIGS. 12A and 12B illustrate a flow chart of an exemplary embodiment of a method of manufacturing the magnetic prosthetic of FIGS. 9-10.
Figure 12B:
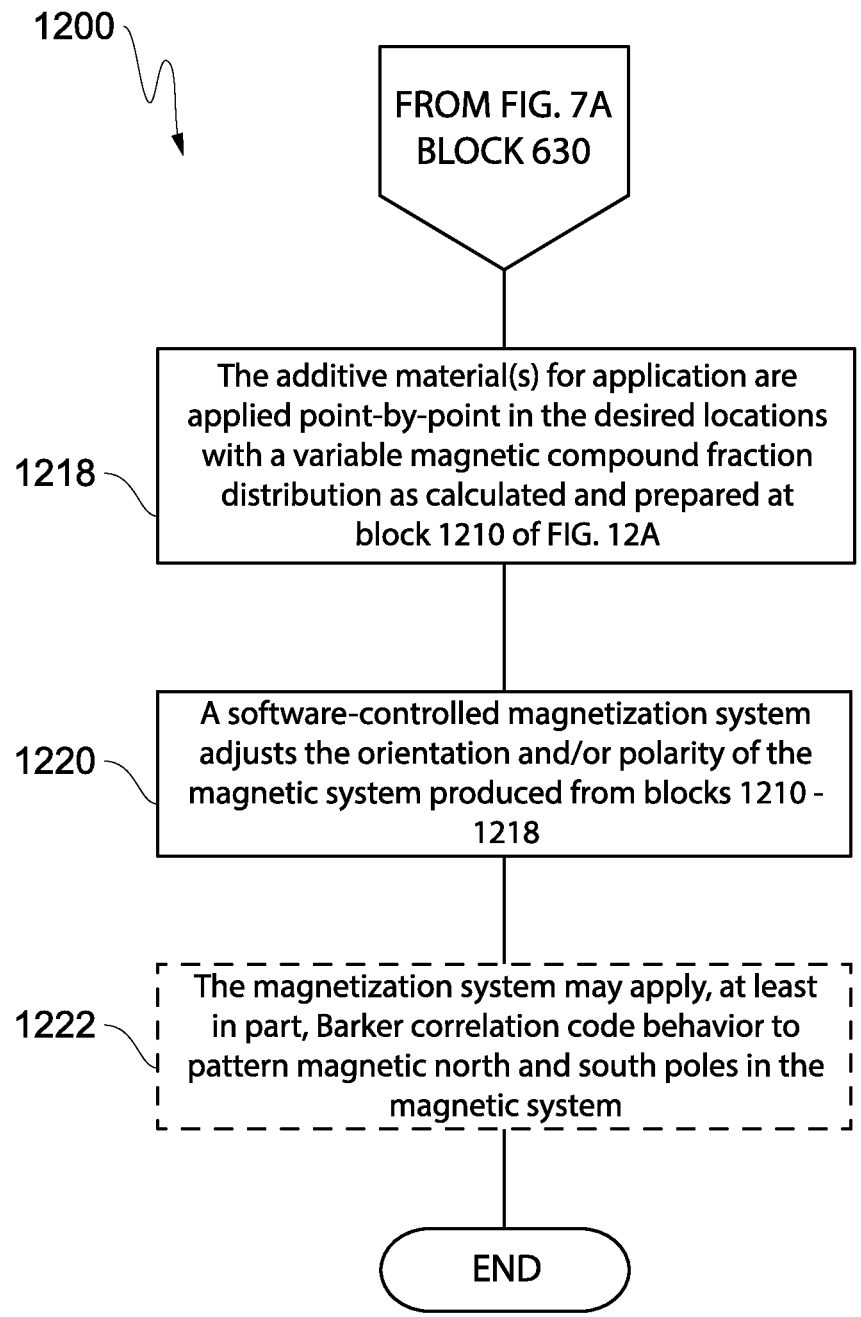

More specifically, at block 1210 of FIG. 12A, a desired geometric shape and magnetic profile for a magnetic system of the prosthetic is computed, designed and planned. At block 1212 of FIG. 12A, a magnetic source material and a substrate material for the prosthetic are compounded and characterized, or prepared to be characterized, for the printing process. At block 1214 of FIG. 12A, a twin-screw mixing extruder is used to mix magnetic filaments/source material with bio-prosthetic preferred substrate material/filaments or other compositions with different concentrations and constituent components. At block 1216 of FIG. 12A, the mixing extruder continuously changes between materials of different concentrations and/or compositions, and a laser diameter measuring system controls the diameter tolerances. At block 1218 of FIG. 12B, the additive material(s) for application are applied point-by-point in the desired locations with a variable magnetic compound fraction distribution as calculated and prepared at block 1210 of FIG. 12A. At block 1220 of FIG. 12B, a software-controlled magnetization system adjusts the orientation and/or polarity of the magnetic system produced from blocks 1210-1218 (before or during manufacture) to enable precision control over the magnetic field of the final product. Optionally, at block 1222 of FIG. 12B, the magnetization system may apply, at least in part, Barker correlation code behavior to pattern magnetic north and south poles in the magnetic system.

Certain steps in the exemplary method described herein naturally precede others for the invention to function as described. However, the invention is not limited to the order of the steps described if such order or sequence does not alter the functionality of the system and method of the present disclosure. That is, it is recognized that some steps may performed before, after, or parallel (substantially simultaneously with) other steps without departing from the scope and spirit of the invention. In some instances, certain steps may be omitted or not performed without departing from the invention. Further, words such as "thereafter", "then", "next", etc. are not intended to limit the order of the steps. These words are simply used to guide the reader through the description of the exemplary method.

Systems, devices and methods for a novel magnetic prosthetic have been described using detailed descriptions of embodiments thereof that are provided by way of example and are not intended to limit the scope of the disclosure. The described embodiments comprise different features, not all of which are required in all embodiments of a magnetic prosthetic according to the solution. Some embodiments of the solution utilize only some of the features or possible combinations of the features. Variations of embodiments of the solution that are described and embodiments of the solution comprising different combinations of features noted in the described embodiments will occur to persons of the art.

It will be appreciated by persons skilled in the art that systems, devices and methods for a novel magnetic prosthetic according to the solution are not limited by what has been particularly shown and described herein above. Rather, the scope of systems, devices and methods a novel magnetic prosthetic according to the solution is defined by the claims that follow.

What is claimed is:

1. An artificial joint prosthesis, comprising:
a first component comprising a first contact surface, a first region within the first component fabricated from at least one polymer including a plurality of magnetic particles embedded in a first polymer matrix; and
a second component comprising a second contact surface, a second region within the second component fabricated from at least one polymer including a plurality of magnetic particles embedded in a second polymer matrix;
wherein the plurality of magnetic particles embedded in at least one of the first polymer matrix and the second polymer matrix is distributed within the surrounding polymer as a variable magnetic fraction comprising a variable composition between approximately 70.0% and approximately 90.0% magnetic material and is configured to create a magnetic field about the artificial joint, directed to facilitate articulation of the artificial joint in vivo.

2. The artificial joint prosthesis of claim 1, wherein the plurality of magnetic particles embedded in at least one of the first polymer matrix and the second polymer matrix is configured within the surrounding polymer as a pattern, shape, bulk geometric structure, or combinations thereof.

3. The artificial joint prosthesis of claim 1, wherein the plurality of magnetic particles embedded in at least one of the first polymer matrix and the second polymer matrix is susceptible to a software-controlled magnetization process to adjust the orientation, or polarity, or combinations thereof.

4. The artificial joint prosthesis of claim 1, wherein the pluralities of magnetic particles embedded in the first polymer matrix and the second polymer matrix, respectively, are configured to create a magnetic field about the first component and the second component, respectively, such that the magnetic field about the artificial joint yields a force curve characterized by repulsion, when the first component and the second component are at or within a distance apart, and attraction, when the first component and the second component are further than the distance apart.

5. An artificial joint prosthesis, comprising:
a first component comprising a contact surface, the contact surface configured as a layer and fabricated from at least one polymer including a plurality of magnetic particles embedded in a first polymer matrix; and
a second component fabricated from at least one polymer including a plurality of magnetic particles embedded in a second polymer matrix;
wherein the embedded magnetic particles in the first and second polymer matrixes comprise a component selected from a group consisting of an iron oxide, an iron alloy, and a rare-earth metal alloy-based material, are encapsulated in a protective coating, and are configured to create a magnetic field about the artificial joint, directed to facilitate articulation of the artificial joint in vivo.

6. The artificial joint prosthesis of claim 5, wherein the protective coating comprises a component selected from a group consisting of natural polymers, synthetic organic polymers, silica, gold, and combinations thereof, with a biocompatible superficial surface.

7. The artificial joint prosthesis of claim 6, wherein the biocompatible superficial surface comprises proteins selected from a group consisting of elastin, collagen, albumin, keratin, fibronectin, silk, silk fibroin, actin, myosin, fibrinogen, thrombin, aprotinin, antithrombin III, and engineered proteins thereof.

8. The artificial joint prosthesis of claim 6, wherein the biocompatible surface comprises an antimicrobial agent selected from the group consisting of triclosan, chlorhexidine, benzalkonium parylene polymer, silver and combinations thereof.

* * * * *